(12) United States Patent
Shaw et al.

(10) Patent No.: US 12,064,605 B2
(45) Date of Patent: Aug. 20, 2024

(54) SYRINGE WITH FLAT INDICIA DISPLAY SURFACE

(71) Applicants: Retractable Technologies, Inc., Little Elm, TX (US); Thomas J. Shaw, Frisco, TX (US)

(72) Inventors: Thomas J. Shaw, Frisco, TX (US); Mark Small, Heavener, OK (US)

(73) Assignee: Retractable Technologies, Inc., Little Elm, TX (US)

( * ) Notice: Subject to any disclaimer, the term of this patent is extended or adjusted under 35 U.S.C. 154(b) by 0 days.

(21) Appl. No.: 16/370,239

(22) Filed: Mar. 29, 2019

(65) Prior Publication Data

US 2019/0298929 A1 Oct. 3, 2019

Related U.S. Application Data

(63) Continuation-in-part of application No. 15/940,305, filed on Mar. 29, 2018.

(51) Int. Cl.
*A61M 5/31* (2006.01)
*A61M 5/315* (2006.01)
*A61M 5/32* (2006.01)

(52) U.S. Cl.
CPC ...... *A61M 5/3129* (2013.01); *A61M 5/31501* (2013.01); *A61M 5/3202* (2013.01); *A61M 5/3234* (2013.01); *A61M 2005/3126* (2013.01); *A61M 2005/314* (2013.01); *A61M 2005/3227* (2013.01); *A61M 2205/3379* (2013.01)

(58) Field of Classification Search
CPC ........ A61M 5/50; A61M 5/178; A61M 5/321; A61M 5/322; A61M 5/3129; A61M 5/3205; A61M 5/3221; A61M 5/3232; A61M 2005/314; A61M 2005/3125; A61M 2005/3126; A61M 2005/3227; A61M 5/3243; A61M 5/3245; A61M 5/3269; A61M 5/3271
See application file for complete search history.

(56) References Cited

U.S. PATENT DOCUMENTS

| 2,117,469 A | 5/1938 | Woodyatt |
| 2,860,635 A | 11/1958 | Wilburn |

(Continued)

FOREIGN PATENT DOCUMENTS

| CN | 102068734 A | 5/2011 |
| CN | 102573959 A | 7/2012 |

(Continued)

*Primary Examiner* — Laura A Bouchelle
(74) *Attorney, Agent, or Firm* — Scheef & Stone, LLP; Robin L. Barnes; Mike Schofield

(57) ABSTRACT

A syringe for medical use having a barrel with a longitudinally extending tubular fluid chamber and at least one longitudinally extending, outwardly facing, substantially flat indicia display surface disposed proximally to the fluid chamber, a plunger slidably inserted into the fluid chamber, a needle projecting forwardly from the barrel in fluid communication with the fluid chamber; and a fixed length needle safety device having an activation handle slidably engaging the barrel and a forwardly projecting needle tip shield encircling the needle that moves forwardly to cover a tip end of the needle when the activation handle is moved forwardly following use of the syringe.

31 Claims, 16 Drawing Sheets

(56) References Cited

U.S. PATENT DOCUMENTS

| | | | |
|---|---|---|---|
| 4,573,976 A | 3/1986 | Sampson et al. | |
| 4,650,468 A | 3/1987 | Jennings, Jr. | |
| 4,702,738 A | 10/1987 | Spencer | |
| 4,790,828 A | 12/1988 | Dombrowski et al. | |
| 4,840,619 A | 6/1989 | Hughes | |
| D302,726 S | 8/1989 | Schwobel | |
| 4,915,696 A | 4/1990 | Feimer | |
| 4,946,447 A * | 8/1990 | Hardcastle | A61M 5/3243 604/198 |
| 4,994,034 A | 2/1991 | Botich et al. | |
| 5,037,402 A | 8/1991 | Bartman | |
| 5,049,133 A | 9/1991 | Villen Pascual | |
| 5,053,010 A | 10/1991 | McGary et al. | |
| 5,084,018 A | 1/1992 | Tsao | |
| 5,092,461 A | 3/1992 | Adam | |
| 5,215,534 A | 6/1993 | DeHarde et al. | |
| 5,312,372 A | 5/1994 | DeHarde et al. | |
| 5,407,436 A | 4/1995 | Toft et al. | |
| 5,437,647 A | 8/1995 | Firth et al. | |
| 5,445,618 A | 8/1995 | Adobbati | |
| 5,456,668 A * | 10/1995 | Ogle, II | A61M 25/0631 604/110 |
| D377,687 S | 1/1997 | Udovch | |
| 5,672,161 A * | 9/1997 | Allen | A61M 5/3269 604/263 |
| 5,782,804 A | 7/1998 | McMahon | |
| D420,129 S | 2/2000 | McMahon | |
| 6,090,077 A | 7/2000 | Shaw | |
| 6,213,987 B1 * | 4/2001 | Hirsch | A61M 5/3269 604/263 |
| 6,416,323 B1 | 7/2002 | Grenfell et al. | |
| 6,514,261 B1 | 2/2003 | Randall et al. | |
| 6,585,690 B1 | 7/2003 | Hoeck et al. | |
| D601,242 S | 9/2009 | Bierman et al. | |
| D601,243 S | 9/2009 | Bierman et al. | |
| D673,670 S | 1/2013 | Linnenschmidt | |
| 8,372,044 B2 * | 2/2013 | Westbye | A61M 5/326 604/110 |
| D693,003 S | 11/2013 | Wang | |
| 9,044,552 B2 | 6/2015 | Schraga | |
| 9,173,726 B2 | 11/2015 | Sabourin | |
| 9,381,309 B2 | 7/2016 | Shaw et al. | |
| 9,623,192 B2 | 4/2017 | Chin et al. | |
| D792,969 S | 7/2017 | Taylor | |
| D793,549 S | 8/2017 | Defusco | |
| D793,550 S | 8/2017 | Defusco | |
| 9,814,841 B2 | 11/2017 | Shaw et al. | |
| D805,199 S | 12/2017 | Chen et al. | |
| D812,748 S | 3/2018 | Funakoshi et al. | |
| D814,630 S | 4/2018 | Finke et al. | |
| D815,732 S | 4/2018 | Mills et al. | |
| D823,457 S | 7/2018 | Shaw et al. | |
| D823,461 S | 7/2018 | Shaw et al. | |
| D829,891 S | 10/2018 | Shaw et al. | |
| D832,423 S | 10/2018 | Ishida | |
| 10,086,141 B2 | 10/2018 | Steel et al. | |
| D835,265 S | 12/2018 | Inoue | |
| 10,525,207 B2 | 1/2020 | Zivkovic et al. | |
| 11,246,989 B1 * | 2/2022 | Halbach | A61M 5/46 |
| 2002/0065488 A1 | 5/2002 | Suzuki et al. | |
| 2002/0068907 A1 | 6/2002 | Dysarz | |
| 2002/0082560 A1 | 6/2002 | Yang | |
| 2003/0028171 A1 | 2/2003 | DeHarde | |
| 2003/0038171 A1 | 2/2003 | Lim et al. | |
| 2005/0020988 A1 | 1/2005 | Woehr et al. | |
| 2005/0159706 A1 | 7/2005 | Wilkinson et al. | |
| 2006/0264825 A1 | 11/2006 | Westbye et al. | |
| 2007/0276338 A1 | 11/2007 | Shue et al. | |
| 2008/0114306 A1 | 5/2008 | Bare | |
| 2012/0004621 A1 | 1/2012 | Shaw et al. | |
| 2012/0022464 A1 | 1/2012 | Zivkovic et al. | |
| 2013/0023826 A1 | 1/2013 | Ishida | |
| 2014/0012206 A1 | 1/2014 | Shaw et al. | |
| 2015/0073303 A1 | 3/2015 | Shaw et al. | |
| 2015/0196714 A1 | 7/2015 | Creaturo | |
| 2015/0202373 A1 | 7/2015 | Creaturo | |
| 2015/0231335 A1 * | 8/2015 | Creaturo | A61M 5/31 604/189 |
| 2022/0054764 A1 | 2/2022 | Shaw et al. | |

FOREIGN PATENT DOCUMENTS

| | | |
|---|---|---|
| CN | 104368068 A | 2/2015 |
| CN | 108619594 A | 9/2018 |
| CN | 108619594 A | 10/2018 |
| DE | 4323466 | 7/1993 |
| JP | 2010098323 | 2/2010 |
| JP | 2016529078 | 9/2016 |
| WO | WO2013050475 | 4/2013 |
| WO | 2016055620 A1 | 4/2016 |
| WO | WO2016176523 | 11/2016 |

* cited by examiner

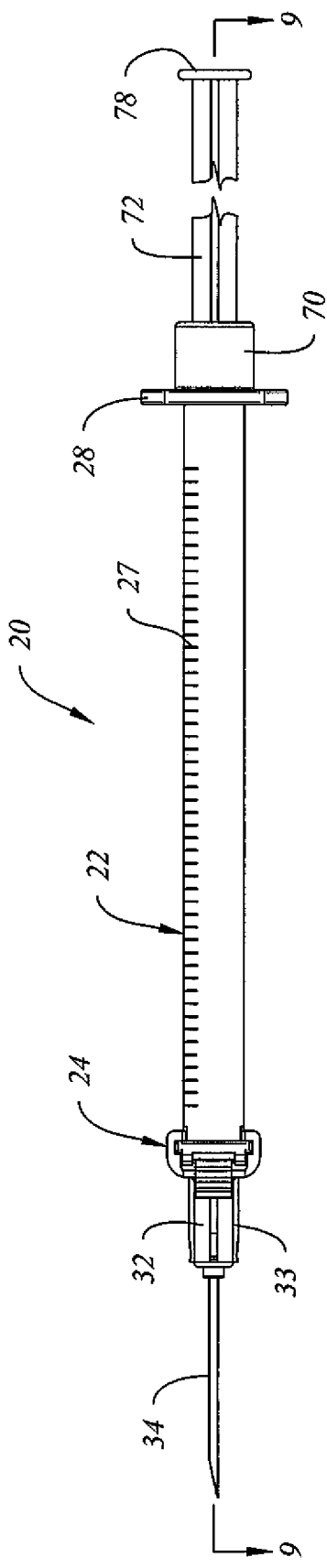
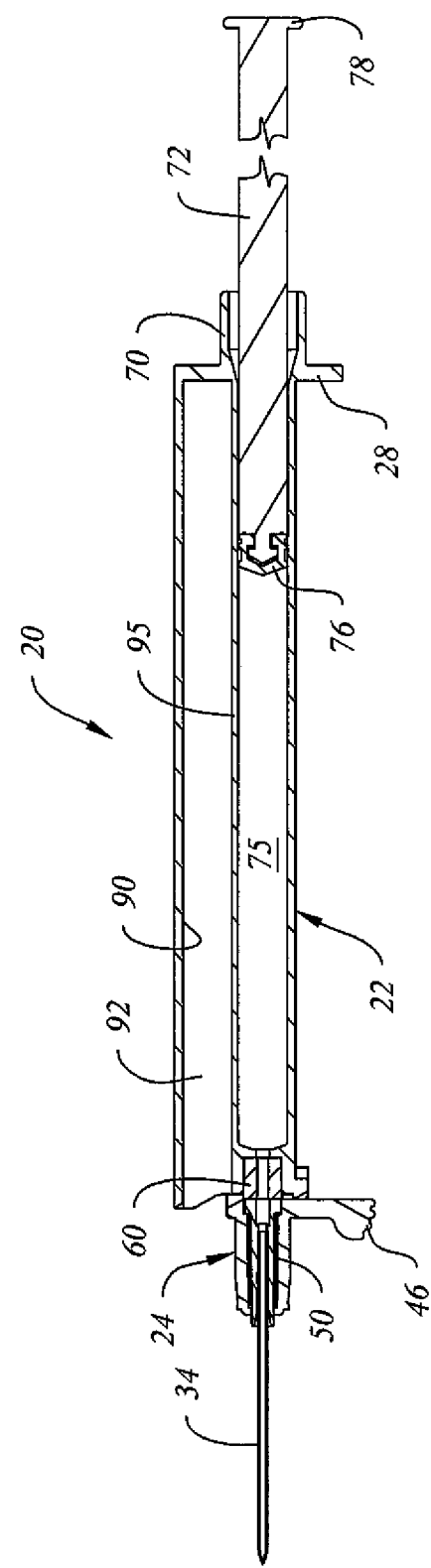
FIG. 8
FIG. 9

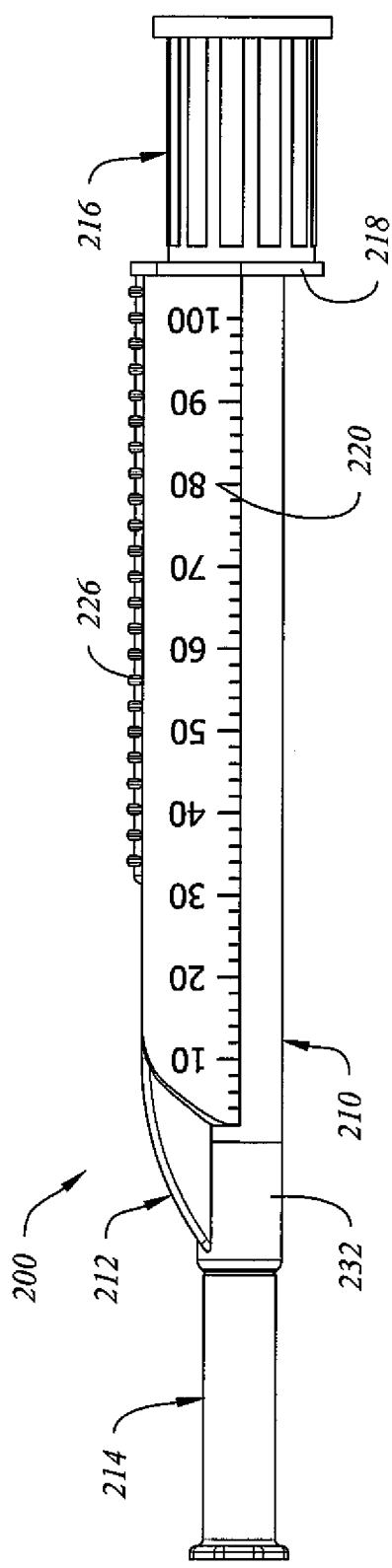

SYRINGE WITH FLAT INDICIA DISPLAY SURFACE

BACKGROUND OF THE INVENTION

1. Field of the Invention

This invention relates to a syringe configured for medical use in aspirating or injecting fluids. The syringe desirably includes a barrel, a plunger slidably engaging a portion of the barrel, and a forwardly projecting needle. The barrel desirably has a substantially tubular inside surface, which functions as a side wall of a fluid chamber, and a longitudinally extending, substantially flat indicia display surface disposed on at least one side of the barrel. Preferably, the subject syringe includes two opposed, outwardly facing, longitudinally extending, substantially flat indicial display surfaces suitable for use in printing dosage scales on the syringe.

One embodiment of the invention also includes a needle retraction mechanism and a laterally offset needle retraction cavity that is substantially coextensive with the length of the fluid chamber of the barrel. The needle is selectively retracted following an injection by sliding the barrel and needle retraction cavity transversely relative to the needle, thereby moving the needle retraction cavity laterally into coaxial alignment with the needle. The substantially full-length, laterally offset needle retraction cavity facilitates the optional use of longer retractable needles than are usable with conventional safety syringes having retractable needles and broadens the range of uses and procedures that are performable with the device without increasing the overall length of the syringe. Depending upon needle length, such uses and procedures can include, for example, performing spinal taps, administering epidural anesthesia, aspirating cysts, and the like, as well as for administering intradermal, subcutaneous or intramuscular injections.

Another aspect of the invention relates to a syringe having a barrel comprising a substantially cylindrical fluid chamber, a needle retraction cavity disposed in parallel and laterally spaced-apart relation to the fluid chamber, and at least one substantially flat, outwardly facing display surface to which indicia such as dosage scales can be applied using a conventional pad printing process. Still another aspect of the invention relates to a syringe having a barrel with two oppositely facing, substantially flat surfaces on which the same or different indicia can be pad printed without having to rotate the barrel, even when printing on 1 mL, 0.5 mL or smaller syringes. The substantially flat display surfaces also facilitate the application of indicia to a syringe by other processes such as embossing, injection molding, and the like.

Another aspect of the invention relates to a medical syringe comprising a barrel and plunger as disclosed above in combination with a frontal attachment having a forwardly projecting, rearwardly biased needle. The frontal attachment and barrel are desirably cooperatively configured so that the frontal attachment slidably engages a front portion of the barrel along an axis that is transverse to the longitudinal axis through the needle.

Another embodiment of the invention as described above embodies a needle safety device having a needle tip shield that extends circumferentially around and is desirably coaxially aligned with the needle. The needle tip shield is desirably connected to or unitarily molded together with an elongate activation handle that is also part of the needle safety device and slidably engages the barrel. The needle safety device of this embodiment of the invention eliminates the need for having a needle retraction mechanism and a needle retraction cavity, and does not require transverse sliding movement of the barrel relative to the needle to protect users from accidental needle sticks. Following use of this embodiment of the syringe, the needle tip shield is selectively advanced to protect the user from the forwardly projecting needle tip by applying manual pressure to a touch surface of the activation handle that is located rearwardly of the needle and needle tip shield. The activation handle slidably engages the syringe barrel and is forwardly slidable relative to the barrel from a first position, in which the needle tip is uncovered, to a second position in which the needle tip is surrounded and protected against inadvertent needle sticks by the needle tip shield. Because the forwardly slidable needle safety device of this embodiment embodies a stop surface that prevents subsequent rearward movement of the device relative to the barrel of the syringe, the user is protected against subsequent accidental exposure of the needle tip and associated needle stick injuries. This embodiment of the invention combines the advantages of flat, printable surfaces having more easily readable dosage indicia with the cost advantages of a simpler but still effective and easy-to-use needle safety device to provide a safe and more affordable solution, particularly for persons needing frequent injections to treat various chronic health conditions. Furthermore, because the dosage markings and indicia are more easily readable by the user, there is less risk of administering an incorrect dosage of a medicinal fluid to a patient and thereby less risk of causing other unintended consequences.

2. Description of Related Art

Syringes intended for medical use typically have barrels comprising substantially cylindrical inside and outside walls, meaning that volumetric dosage indicia or other markings are applied to an arcuate outer surface during manufacture. This can be difficult, and especially so when the diameter of the barrel and radius of curvature of the outside wall are small (as with 1 mL, 0.5 mL and smaller syringes) and where the available outside surface area is extremely limited, or on syringes where different dosing scales or other indicia are applied to opposite sides of the barrel. In such instances it is often necessary to spin or rotate the barrel while printing, and it is also often difficult to read indicia such as dose measuring lines and the related numeric values or other markings because they wrap so far around the circumference of the barrel and because indicia or markings on one side are often viewable through the syringe and can confuse the user, sometimes leading to the commission of medical errors. For at least these reasons, syringes having substantially flat surfaces for use in applying dosage markings and other indicia are needed.

Medical syringes having rearwardly biased needles that retract into coaxially aligned retraction cavities disposed inside the plunger are known, having previously been disclosed, for example, in U.S. Pat. Nos. 5,049,133; 5,053,010; 5,084,018 and 6,090,077. More recently, medical syringes having frontal attachments containing rearwardly biased needles that retract into needle retraction cavities that are part of the frontal attachment have been disclosed, for example, in U.S. Pat. No. 9,381,309.

Even more recently, medical syringes with frontal attachments have been disclosed that slidably engage barrels having needle retraction cavities unitarily molded together with the barrel and disposed parallel to the fluid chamber. In U.S. Pat. No. 9,814,841 (FIGS. 37-42), for example, the length of the needle retraction cavity is substantially shorter than the length of the fluid chamber inside the barrel and the needle retraction cavity does not cooperate with an outer wall of the barrel to form substantially flat outside surfaces that are adjacent to and substantially coextensive with the fluid chamber.

Other references disclosing devices arguably bearing some degree of similarity to various aspects or embodiments of the invention include the following: U.S. Pat. Nos. 4,573,976; 4,702,738; 4,790,828; 4,915,696; 5,037,402; 5,092,461; 5,215,534; 5,312,372; 9,623,192; U.S. Pub. No. 2002/0065488 A1; U.S. Pub. No. 2003/0038171 A1; and U.S. Pub. No. 2005/0159706 A1

SUMMARY OF THE INVENTION

According to one embodiment of the invention a syringe for medical use is disclosed that comprises a one-piece barrel having a fluid chamber and a laterally offset needle retraction cavity that are substantially parallel and separated by a common wall. The needle retraction cavity can have a non-circular cross-section and is desirably substantially coextensive in length with the fluid chamber, thereby facilitating the use of longer needles without increasing the overall length of the barrel in order to accommodate retraction of the longer needles as is the case with safety syringes that retract the needle into the barrel following use. The barrel further comprises an outer wall having at least one substantially flat, outwardly facing display surface upon which indicia such as a volumetric dosage scale, for example, can be applied using conventional pad printing technology or another similarly effective alternative means. The at least one substantially flat display surface is desirably disposed proximally to the fluid chamber and also desirably comprises a measurement scale that is longitudinally aligned with at least that portion of the fluid chamber that is useful for injecting or aspirating a fluid. According to one preferred embodiment of the invention, two oppositely facing, longitudinally coextensive, substantially flat surfaces are provided, with each surface spanning at least a portion of an external wall of the fluid chamber and at least a portion of the external wall of the needle retraction cavity.

The subject invention is particularly useful with syringes having usable volumes of 1 mL or less, which syringes typically have smaller barrel diameters that cause the volumetric dosage indicia applied to the outside surface to wrap around a greater portion of the circumference of the barrel. According to another preferred embodiment of the invention, pad printing technology (sometimes referred to as "tampography") is used to apply volumetric dosage indicia or other markings to the substantially flat display surface of the syringe. The needle retraction cavity can be made (preferably molded from a suitable polymeric material) with a non-circular cross-section and is offset laterally from the barrel to facilitate creation of a wider, outwardly facing, substantially flat display surface during manufacture. The substantially flat display surface desirably comprises at least one side that is proximal to the fluid chamber of the barrel and thereby provides an opportunity, if desired, for molding volumetric dosage markings or other indicia onto the otherwise flat display surface or embossing the indicia on or into the display surface.

Another embodiment of the subject syringe comprises a barrel and plunger as disclosed above in combination with a frontal attachment having a forwardly projecting, rearwardly biased needle. The frontal attachment and barrel are desirably cooperatively configured so that the frontal attachment slidably engages a front portion of the barrel along an axis that is transverse to the longitudinal axis through the needle. When the syringe is disposed in the use position, the needle is aligned with a first opening in the front of the barrel that is communicates with a substantially cylindrical fluid chamber inside the barrel to establish a coaxially aligned fluid flow path between the fluid chamber and the needle. A fluid seal is desirably seated around the first opening to resist fluid leakage between the frontal attachment and the barrel. The needle retraction cavity extends rearwardly from a second opening in the front of the barrel. in parallel and spaced-apart relation to the fluid chamber in the barrel, and desirably shares a common wall with at least a portion of fluid chamber. Following use of the syringe, relative transverse movement between the barrel and the frontal attachment repositions the rearwardly biased needle into alignment with the needle retraction cavity, thereby releasing the needle to be forced by the biasing means, typically a compressed spring, into a retracted position wherein the needle no longer projects forwardly from the syringe.

Another embodiment of the subject syringe embodies wider, substantially flat display surfaces disposed on a medical syringe having a unitary barrel and needle retraction cavity that cooperate with substantially flat edge portions of the surrounding flange to help prevent the syringe from rolling off a tray or other flat surface. The substantially flat surfaces also allow the flange around the barrel to be proportionally narrower as compared to the flanges of conventional syringes having tubular barrels and still provide larger surface areas that are more easily graspable by a user. The oppositely facing, substantially flat surfaces also improve stability and the degree of control that can be exercised over the syringe by a user during an injection or other procedure. Because the subject syringe has a barrel with a laterally offset needle retraction cavity that can be molded integrally with the fluid chamber, at least one, and preferably two (oppositely facing), substantially flat, outwardly facing surface areas are provided that are useful for the placement of an array comprising a volumetric scale or other indicia that are easily readable by the user and thereby reduce the likelihood of dosing errors during aspiration or injection.

Another embodiment of the invention comprises the subject syringe in combination with a selectively releasable needle cover that can also comprise a locking member configured to engage a portion of the barrel and resist sliding lateral movement of the barrel relative to the frontal attachment to prevent accidental retraction of the needle prior to using the syringe. Retraction of the needle following use of the syringe reduces the likelihood of reusing the syringe or of accidental needle sticks and the inadvertent transmission of blood-borne pathogens.

Another embodiment of the invention comprises the subject syringe in combination with a plunger cap that is releasably attached to the rear portion of the syringe, typically behind the finger flange, and is selectively removable prior to fluid aspiration or use. When both the needle cover and the plunger cap are in place, the needle and the internal, fluid-contacting portions of the syringe are enclosed and protected from contamination whether or not the syringe is also enclosed inside another package. Because of this, the syringes can be assembled and shipped in bulk prior to packaging and sterilization.

Although the subject syringe is especially useful in administering relatively small doses of a medicinal fluid such as insulin or a vaccine to a user by injection or infusion, the structure and operation of the apparatus is not limited to particular sizes, doses or procedures. For example, syringes configured as disclosed here can also be configured for use in aspirating fluid samples from patients during clinical procedures such as knee or spinal taps. Because the overall syringe length is reduced through use of the disclosed frontal attachment in combination with the novel barrel of the invention, longer needles can be used and still be retracted into the syringe following use. As used in this disclosure, "retracted" or "retraction" refer to the process by which a needle is moved from a forwardly projecting use position to a post-use position in which the needle point no longer projects forwardly from the frontal attachment, no matter whether the force acting upon the needle is pushing or pulling the needle tip rearwardly from the forwardly projecting position.

Another embodiment of a syringe for medical use is disclosed having a barrel with a longitudinally extending tubular fluid chamber and at least one longitudinally extending, outwardly facing, substantially flat indicia display surface disposed proximally to the fluid chamber, a plunger slidably inserted into the fluid chamber, a needle projecting forwardly from the barrel in fluid communication with the fluid chamber; and a needle safety device of fixed, predetermined length. The needle safety device desirably includes an activation handle slidably engaging the barrel and a forwardly projecting needle tip shield encircling the needle. In a first stop position, the needle tip shield is disposed around a nose portion of the barrel. In a second stop position, the activation handle is moved forwardly under manual pressure following use of the syringe, causing the needle tip shield to move forwardly to circumferentially surround and cover a tip end of the needle.

Another embodiment of the invention is disclosed that desirably embodies one and preferably two oppositely facing, substantially flat indicia display surfaces and also embodies a needle safety device having a needle tip shield that extends circumferentially around the needle and is desirably coaxially aligned with the needle. The needle tip shield is attached or connected to, or unitarily molded together with, an activation handle that slidably engages the barrel. Suitable rails, ramps, stop shoulders and detents or other similarly effective means are desirably provided as part of the needle safety device and the barrel so that the activation handle can be advanced smoothly and without substantial interference when desired, and will not accidentally retract afterward to expose the needle tip. The needle safety device of this embodiment of the invention eliminates the need for having a needle retraction mechanism, a needle retraction cavity or any transverse sliding movement of the barrel relative to the needle to protect users from accidental needle sticks. Following use of the syringe, the needle tip shield is selectively advanced to protect the user from the forwardly projecting needle tip by applying manual pressure to a touch surface of the activation handle that is located rearwardly of the needle and needle tip shield. The activation handle slidably engages the syringe barrel and is forwardly slidable relative to the barrel from a first position, in which the needle tip is uncovered, to a second position in which the needle tip is surrounded and protected against inadvertent needle sticks by the needle tip shield. The needle tip is desirably disposed sufficiently inside the needle tip shield once the needle safety device is fully extended relative to the barrel that someone handling the used syringe will not inadvertently be subjected to a needle stick injury by simply placing a fingertip over the end of the syringe.

In another embodiment of the invention, the activation handle further comprises a manually engageable touch surface.

In another embodiment of the invention, the barrel and the activation handle comprise cooperatively engageable elements that enable manually actuated and controllable, longitudinally slidable movement of the activation handle relative to the barrel between two predetermined stop positions. The first stop position is a fully retracted use position in which the needle tip shield substantially surrounds the nose. The second stop position is a fully extended post-use position in which the needle tip shield circumferentially surrounds a tip end of the forwardly projecting needle.

In one preferred embodiment of the invention, the forwardly projecting needle is disposed in fixed relation to the nose of the barrel but it will be appreciated upon reading this disclosure that a similarly configured syringe can be made with needles configured to be selectively attachable to the barrel.

These and other features of the present invention will be better understood from a consideration of the following detailed description of various embodiments and appended claims in conjunction with the accompanying drawings.

BRIEF DESCRIPTION OF THE DRAWINGS

The syringe of the invention is further described and explained in relation to the following drawings wherein:

FIG. 8 is a right side elevation view of the embodiment of FIG. 4 with the plunger cap removed and with the plunger withdrawn to an aspirated position;

FIG. 9 is a cross-sectional view taken along line 9-9 of FIG. 8;

FIG. 18 is a side elevation view of the syringe embodiment of FIG. 14;

FIG. 19 is a top plan view of the syringe embodiment of FIG. 14;

It should be noted that the drawings are not necessarily to scale.

DESCRIPTION OF PREFERRED EMBODIMENTS

Figure 1:
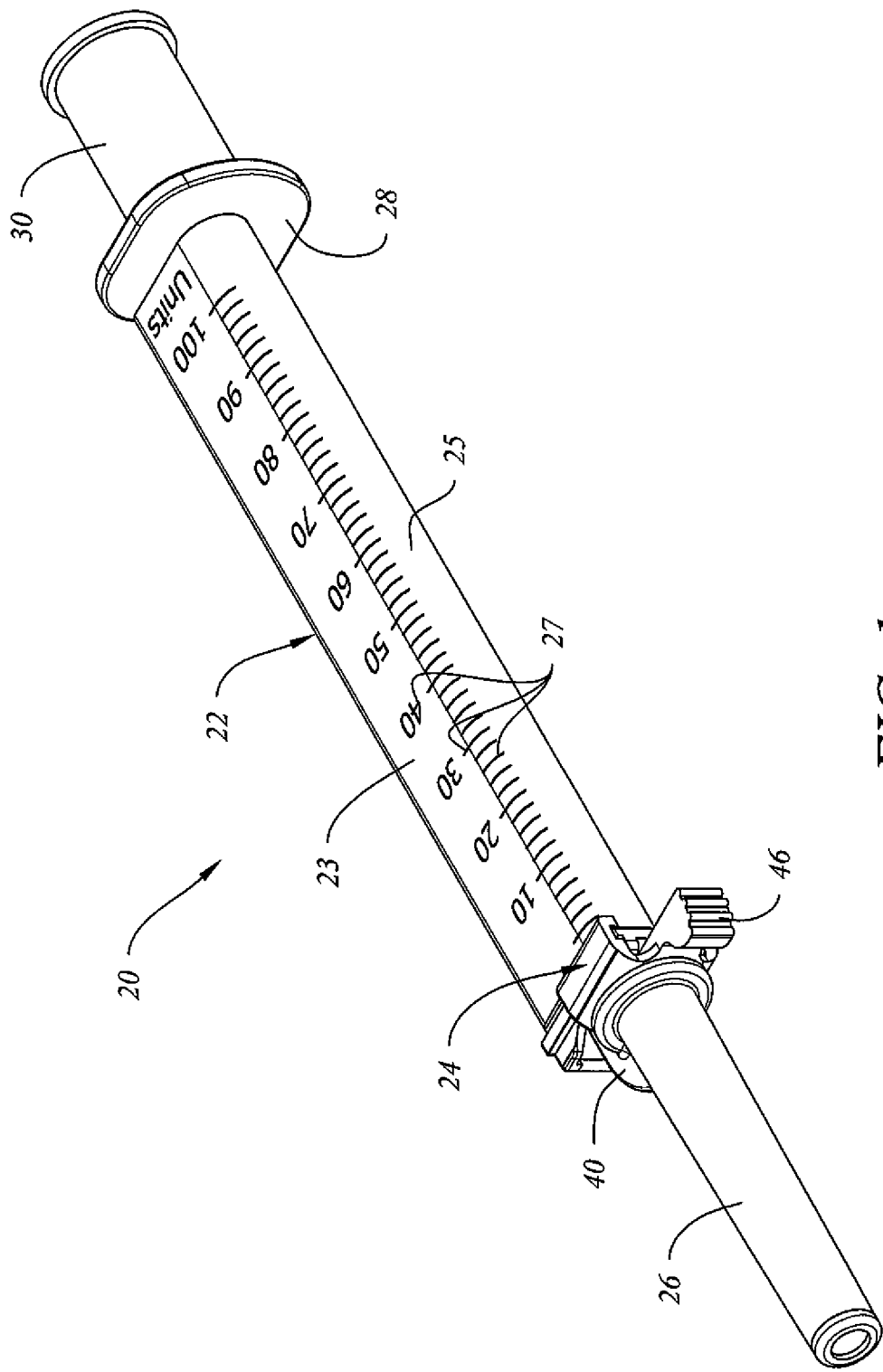
FIG. 1 is a top front perspective view of one embodiment of the invention in which the needle cover (including the locking member) and the plunger end cap are installed in the position in which the subject syringes can be packaged, shipped and stored, with the locking member of the needle cover restricting lateral sliding movement of the barrel relative to the frontal attachment prior to use.

Referring to FIG. 1, syringe 20 comprises barrel 22 further comprising substantially flat display surface 23, frontal attachment 24, outside wall 25 of fluid chamber 75 (visible in FIG. 9), selectively removable needle cover 26, an array of volumetric measuring indicia 27, finger flange 28, removable plunger cap 30 and locking member 40. As shown in FIG. 1, the principal volumetric measuring indicia 27 are applied to display surface 23, including for example at least the Arabic numerals identifying the number of fluid units and the associated principal measurement indicia. It should be appreciated, however, that the accompanying figures of the drawings are for illustrative purposes and are not drawn to scale and that placement of some features such as the secondary unit markings 27 relative to substantially flat display surface 23 can vary from the positions shown. At least a portion of each secondary (individual) unit indicia or markings desirably commences on display surface 23 or proximal to the edge of display surface 23, and optionally continues for a short distanced onto the curved outer wall of fluid chamber 25. Such placement is understood to be within the operational capabilities of conventional pad printing technology that is now readily available to those of ordinary skill in the art.

As depicted in FIG. 1, syringe 20 has frontal attachment 24 shown in the "pre-use" configuration with needle cover 26 and locking member 40 in place to prevent frontal attachment 24 from shifting laterally relative to barrel 22 prior to use because of pressure inadvertently applied to textured touch pad 46 or to the opposite side of barrel 22. Removable plunger cap 30 is also installed behind finger flange 28 to prevent the plunger (not visible) from being accidentally withdrawn from barrel 22 and to prevent inadvertent contamination inside the rear opening of barrel 22 or around the rearwardly extending handle portion of the plunger, as seen in FIG. 9, which is discussed below.

Figure 2:
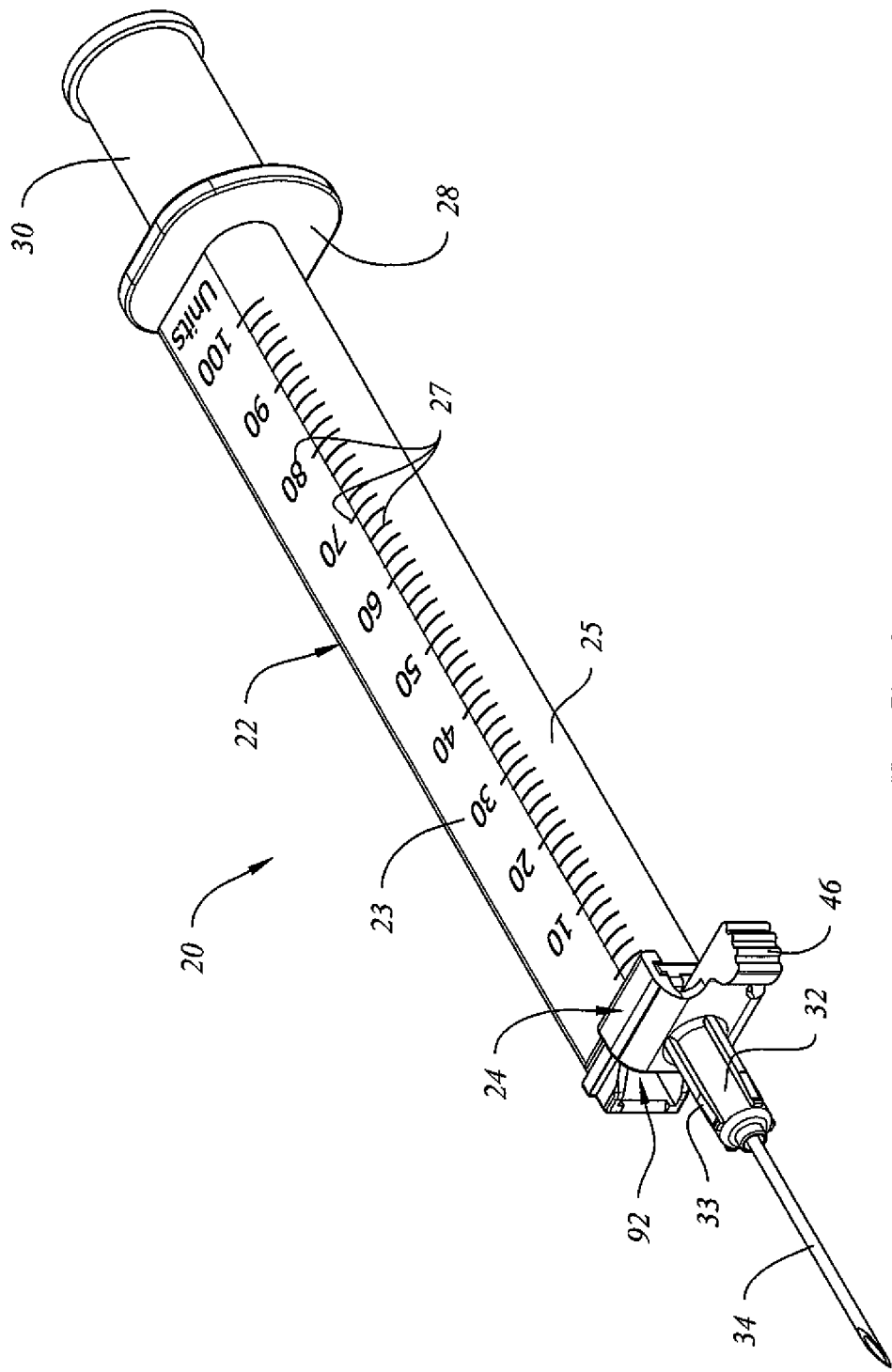
FIG. 2 is a top front perspective view of the embodiment of FIG. 1 in which the needle cover is removed.

Referring to FIGS. 2, 4-5 and 12, barrel 22 and frontal attachment 24 of syringe 20 are shown in the same position as in FIG. 1 except that needle cover 26 (with locking member 40) is removed. The front opening into needle retraction cavity 92 is more clearly visible, and needle 34 is also visible, projecting forwardly from needle support member 32 of frontal attachment 24. Circumferentially spaced, axially tapered ribs 33 are disposed around needle support member 32 and provide surfaces for frictional engagement with the inside surface of needle cover 26 prior to removal. In FIG. 2, needle 34 is desirably coaxially aligned with the longitudinal axis through fluid chamber 75 (FIG. 9).

Figure 3:
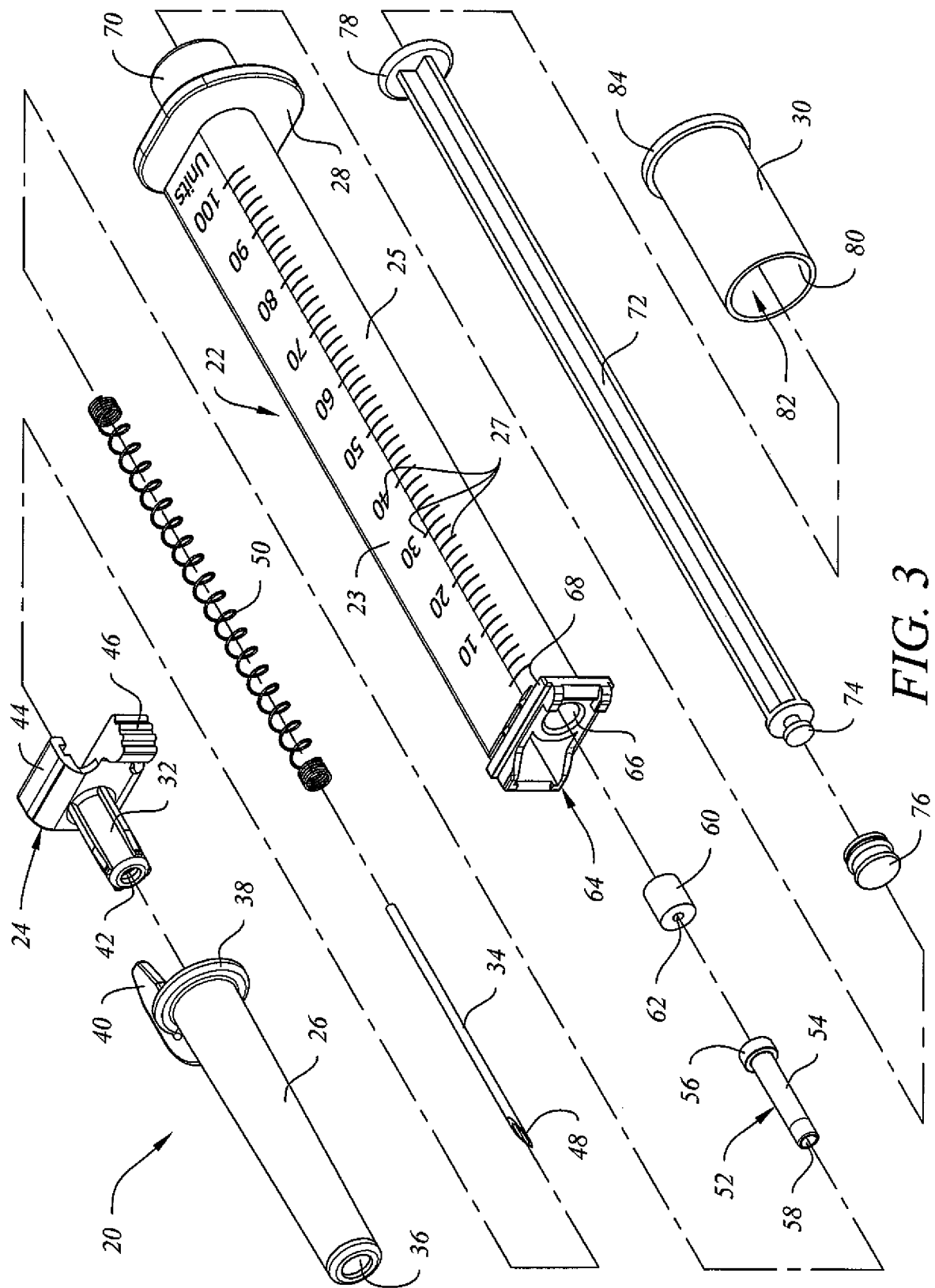
FIG. 3 is an exploded top front perspective view of the embodiment of FIG. 1.

Referring to FIG. 3, needle cap 26 of syringe 20 further comprises a forwardly facing, inwardly tapered, substantially cylindrical sidewall having front end 36, rearwardly facing annular collar 38, and locking member 40 projecting rearwardly past annular collar 38. Frontal attachment 24 further comprises forwardly projecting, substantially tubular needle support member 32 with front opening 42, upper guide member 44, lower guide member 45 (visible in FIG. 7), and laterally projecting textured touch pad 46.

Syringe 20 desirably includes needle 34 with forwardly facing beveled needle tip 48, and a needle retraction mechanism further comprising coiled compression spring 50 and needle holder 52. Needle holder 52 further comprises an elongated shaft 54 with tubular bore 58 that is insertable into the rear of spring 50. The diameter of head 56 of needle holder 52 is sufficiently greater than the inside diameter of spring 50 that spring 50 can be held in compression by head 56 when frontal attachment 24 is slidably engaged with front portion 64 of barrel 22 as discussed in relation to FIGS. 6 and 7 below. The rear end of needle 34 is insertable into tubular bore 58 of needle holder 52 and attachable in fixed relation to the inside of elongated shaft 54 by any suitable, commercially available means such as an adhesive. Although a needle retraction mechanism as disclosed here is satisfactory for use in syringe 20, it will be appreciated that other similarly effective elements and mechanisms useful for rearwardly biasing needle 34 inside syringe 20 can also be used in making the invention.

Still referring to FIG. 3, annular polymeric fluid seal 60 with tubular bore 62 is desirably insertable into recess 66 in front portion 64 of barrel 22 so that the forwardly facing end of seal 60 is disposed in abutting contact with rearwardly facing head 56 of needle holder 52 when the needle retraction mechanism is installed inside frontal attachment 24 and frontal attachment 24 is attached in slidable engagement with front portion 64 of barrel 22. When frontal attachment 24 of syringe 20 is assembled to front portion 64 of barrel 22 during manufacture, a continuous, substantially linear, fluid flow path is established through needle 34, needle holder 52 and annular fluid seal 60 into tubular, longitudinally extending fluid chamber 75 (visible in FIG. 9).

In addition to front portion 64, barrel 22 further comprises substantially flat display surface 23, curved outside wall surface 25, finger flange 28 and rearwardly projecting annular collar 70. During assembly of syringe 20, elastomeric plunger seal 76 is desirably installed on forwardly projecting boss 74 on the front end of plunger handle 72 opposite rearwardly facing plunger thumb pad 78, and plunger handle 72 is then inserted into a rearwardly facing opening defined by annular collar 70. Assembly of syringe 20 is then completed by installing substantially cylindrical plunger cap 30 on the rearwardly facing end of barrel 22. Plunger cap 30 further comprises open front end 80, cylindrical bore 82 and closed rear end 84. Plunger cap 30 is installed around plunger thumb pad 78 and in frictional engagement with the outside wall of annular collar 70. Volumetric measuring indicia 27 applied as discussed in relation to FIG. 1 also appear on the outwardly facing portions of substantially flat display surface 23 and curved outside wall surface 25.

Figure 6:
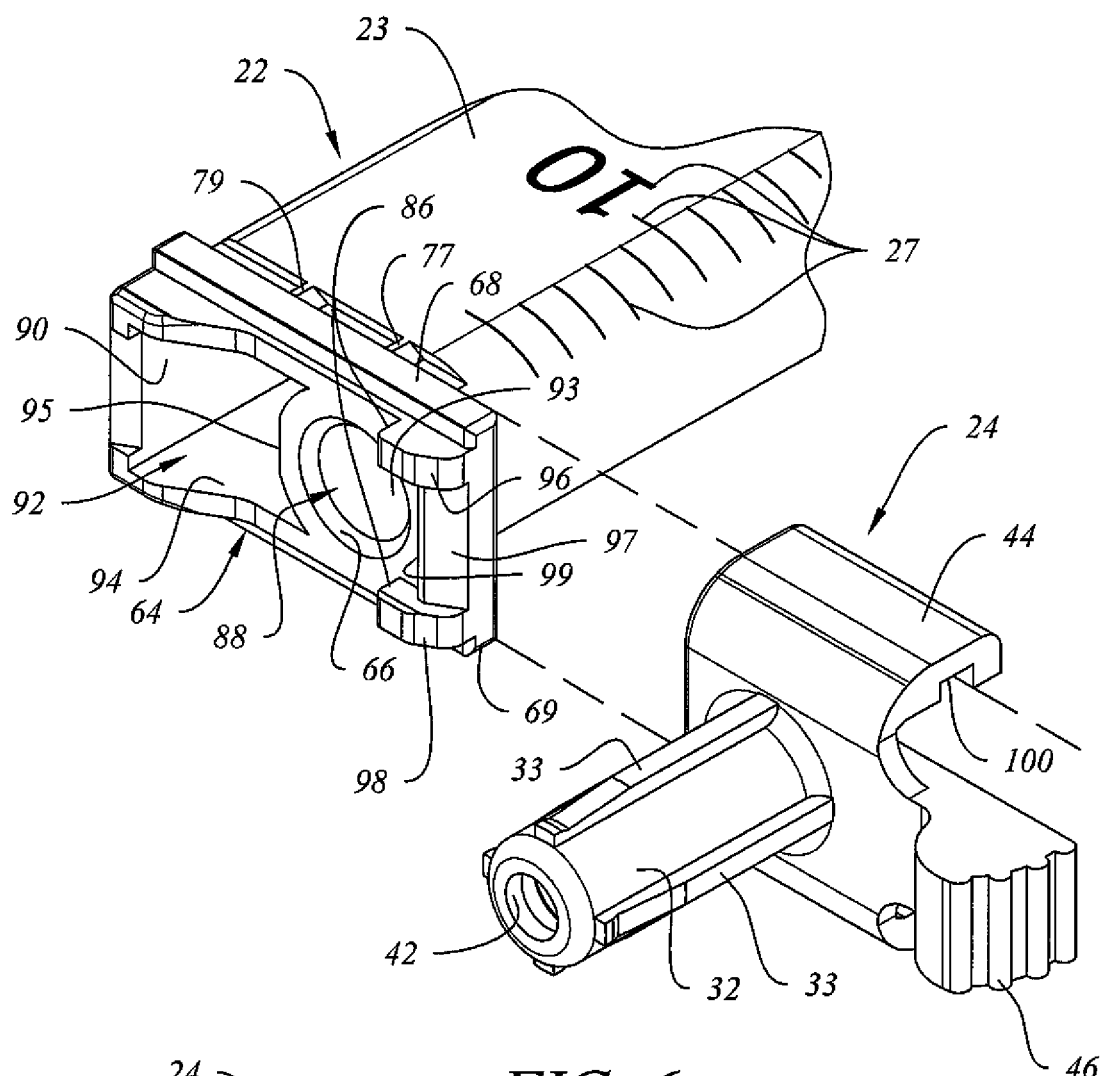
FIG. 6 is an exploded detail perspective view, partially broken away, of the frontal attachment of the embodiment of FIG. 3 shown in juxtaposition to the front portion of the barrel of the embodiment of FIG. 3.
Figure 11:
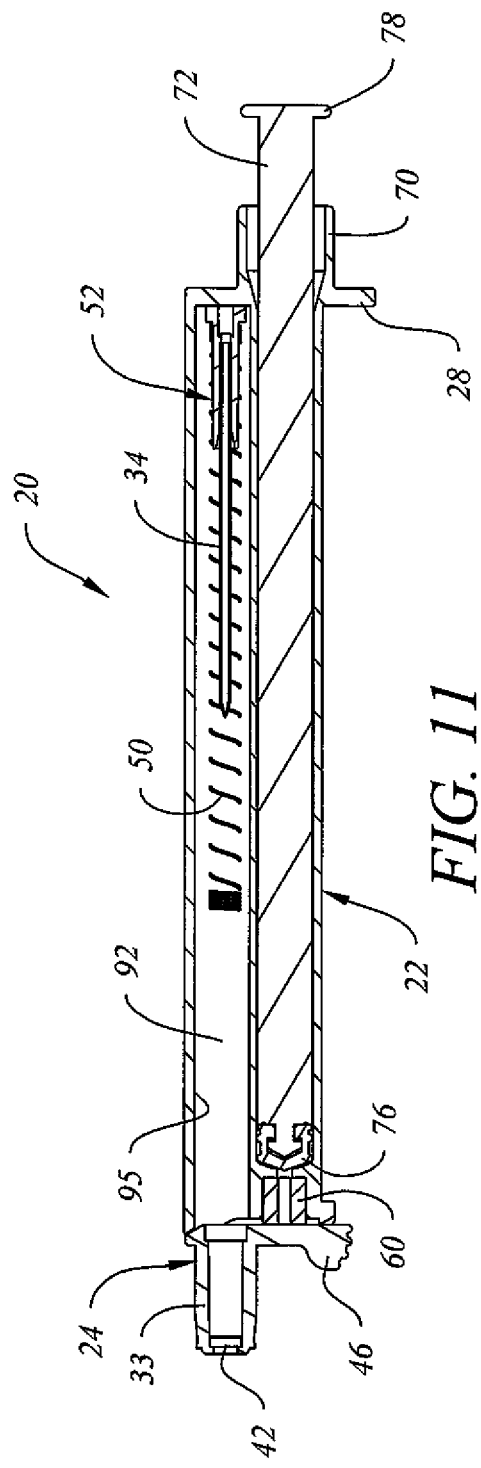
FIG. 11 is a cross-sectional view taken along line 11-11 of FIG. 10.
Figure 12:
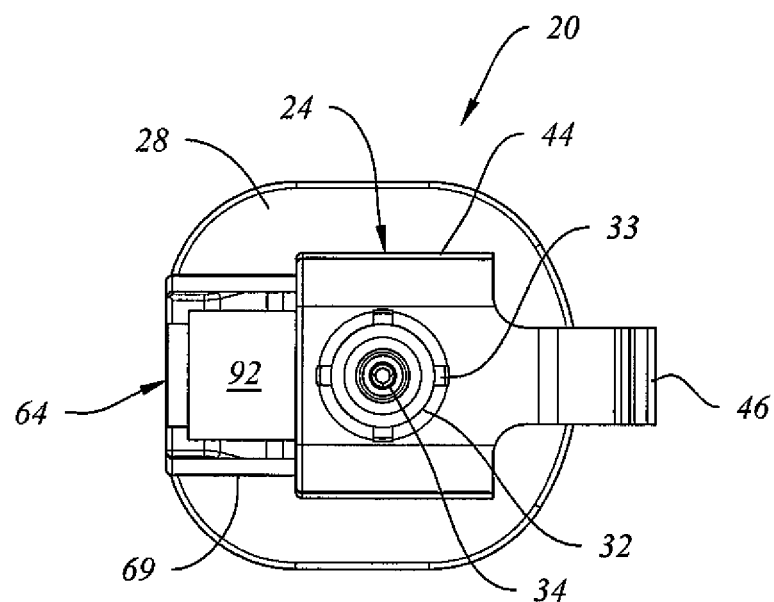
FIG. 12 is a front elevation view of the embodiment of FIG. 2.

FIGS. 3, 6 and 11 further disclose the forwardly facing opening into needle retraction cavity 92 in relation to front portion 64 of barrel 22. Needle retraction cavity 92 has a closed rear end that is adjacent to finger flange 28, and is bounded by side walls 90, 95, bottom wall 94, and a top wall that also includes upwardly facing, substantially flat display surface 23 of barrel 22.

Figure 7:
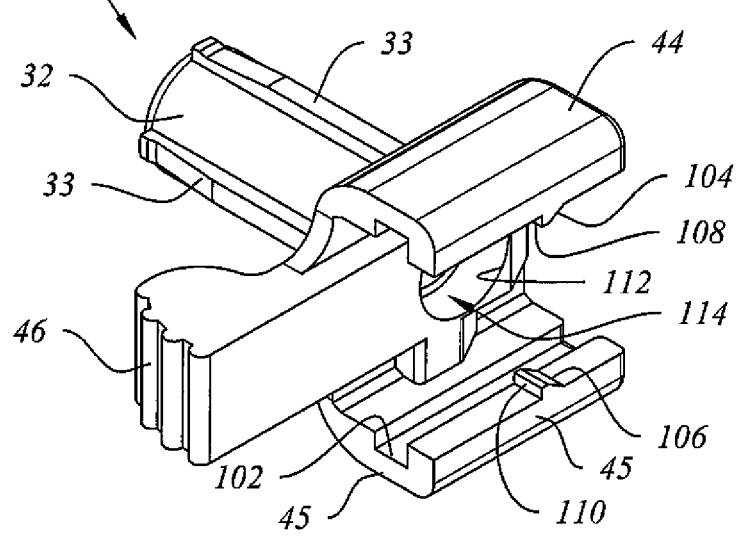
FIG. 7 is a top rear perspective view of the frontal attachment of FIG. 3.

The assembly of frontal attachment 24 to front portion 64 of barrel 22 of syringe 20 is further described and explained in relation to FIGS. 6 and 7. Referring to FIG. 6, annular fluid seal 60 (visible in FIG. 3) is first inserted into recess 66 of front portion 64 of barrel 22. Front portion 64 further comprises laterally extending top rail 68 and bottom rail 69 that are disposed in transverse relation to the longitudinal axis through fluid chamber 75 (FIG. 9) of barrel 22. Rounded attachment guides 96, 98 are disposed forwardly of top and bottom rails 68, 69, respectively, and are configured to facilitate the assembly of frontal attachment 24 to front portion 64 of barrel 22 by passing above and below the arm connecting textured touch pad 46 to the back side of frontal attachment 24.

Referring to FIG. 7, annular opening 112 is provided in the back side of frontal attachment 24 to facilitate insertion of spring 50 and needle holder 52, discussed above in relation to FIG. 3, and spring 50 is desirably compressed between an annular shoulder inside front opening 42 (visible in FIG. 11) and is held in compression behind head 56 of needle holder 52 while frontal attachment 24 is moved into sliding engagement with front portion 64 of barrel 22. Frontal attachment 24 further comprises upper guide 44 having a downwardly facing, laterally extending recess 100 and lower guide 45 having an upwardly facing, laterally extending recess 102. Upper ramp and lower ramp 104, 106, respectively, of frontal attachment 24 are configured to slide over two laterally spaced-apart sets of opposed ramps with blocking shoulders 77, 79 (the lower set not being visible in FIG. 6). Laterally extending top rail 68 and bottom rail 69 of front portion 64 of barrel 22 are desirably cooperatively engaged with upper and lower recesses 100, 102, respectively, by sliding frontal attachment 24 onto front portion 64 of barrel 22 when frontal attachment 24 and front portion 64 are positioned as shown in FIG. 6. As pressure is applied to textured touch surface 46, frontal attachment 24 moves along rails 68, 69 until top and bottom blocking shoulders 108 of upper guide 44 pass over and then drops into facing relation to upper and lower blocking shoulders 77. At this time, needle support member 32 and needle holder 52 (not shown in FIGS. 6 and 7) are desirably coaxially aligned with the longitudinal axis of fluid chamber 75 (visible in FIG. 9). Any attempt to move frontal attachment 24 back to a disconnected position as shown in FIG. 6 will be resisted by facing and abutting contact between upper and lower blocking shoulders 77 of front portion 64 and top and bottom blocking shoulders 108, 110, respectively, of frontal attachment 24.

Figure 4:
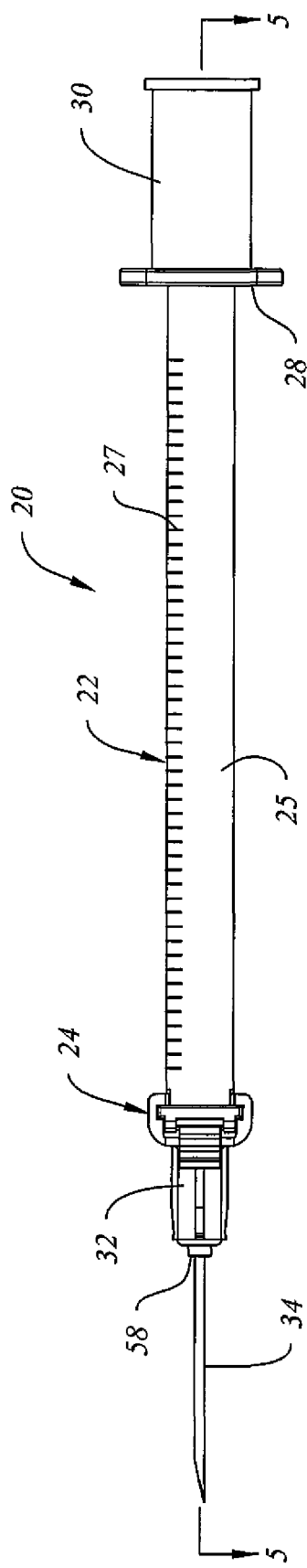
FIG. 4 is a right side elevation view of the embodiment of FIG. 2.
Figure 5:
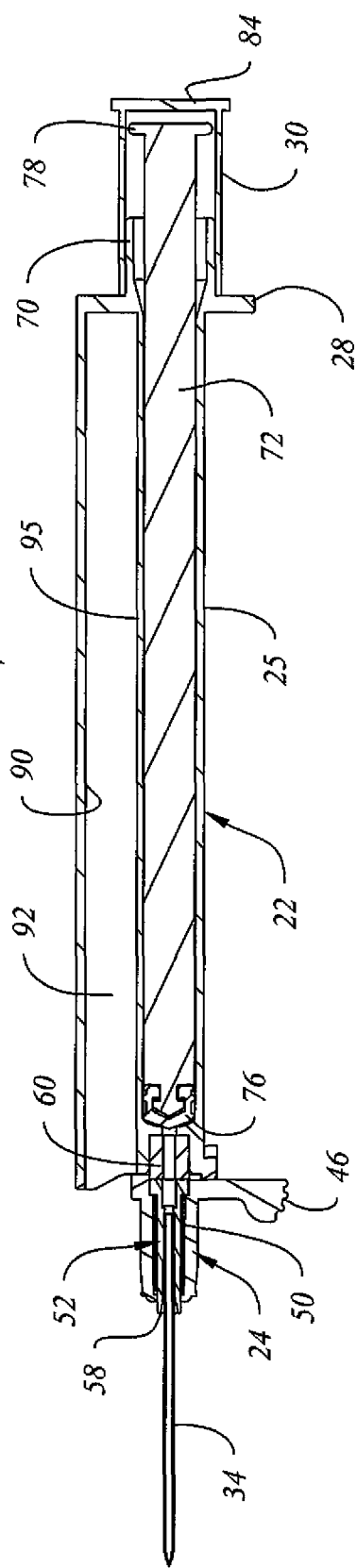
FIG. 5 is a cross-sectional view taken along line 5-5 of FIG. 4.

FIGS. 4 and 5 depict syringe 20 of FIG. 2 with the needle cover removed and with plunger cap 30 still in place and with textured touch surface 46 in the initial position relative to barrel 22 as described above. Needle 34 is installed inside bore 58 of needle holder 52, which is seated inside needle support member 32 of frontal attachment 24, with spring 50 compressed between head 56 (FIG. 3) of needle holder 52. Spring 50 applies a rearwardly directed biasing force to needle holder 52 and needle 34, and is pressed by spring 50 into facing and abutting contact with the front surface of annular fluid seal 60, thereby establishing a coaxially aligned fluid path through needle 34, needle holder 52 and fluid seal 60 into fluid chamber 75 (visible in FIG. 9) of barrel 22. As shown in FIGS. 4 and 5, plunger seal 76 is pushed fully forward into substantially cylindrical fluid chamber 75 of barrel 22.

Referring to FIGS. 8-9, syringe 20 is configured so that fluid can be aspirated into the syringe, with textured touch pad 46 again in the same initial position as previously described. Plunger cap 30 (as seen in FIGS. 2, 4-5) is removed and plunger handle 72 is withdrawn as it would be while aspirating fluid into fluid chamber 75. In FIG. 9 it is seen that needle retraction cavity 92 is substantially coextensive in length with fluid chamber 75, thereby facilitating the placement of volumetric measuring indicia 27 on substantially flat surface 23 (visible in FIG. 3) that facilitates full utilization of the volume of fluid chamber 75 and also facilitating the retraction of needles such as biopsy needles that are often substantially longer than needle 34 (visible inside needle retraction cavity 92 in FIG. 11 below). Once fluid is aspirated into fluid chamber 75, fluid can also be injected into a patient or expelled from fluid chamber 75 by pressing forwardly on plunger thumb pad 78 while applying finger pressure against the forwardly facing side of flange 28.

Figure 10:
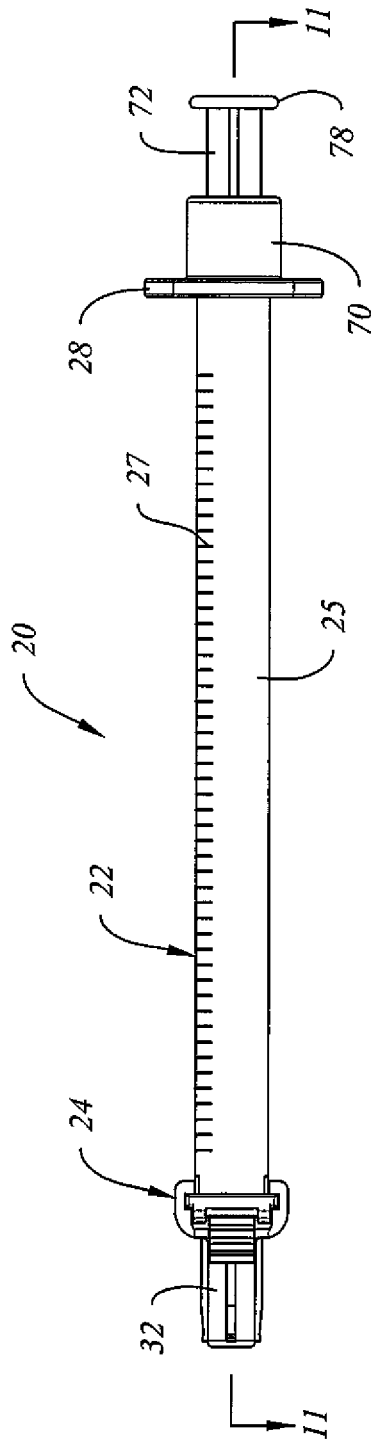
FIG. 10 is a right side elevation view of the embodiment of FIG. 8 with the needle retracted and with the plunger fully advanced inside the barrel.
Figure 13:
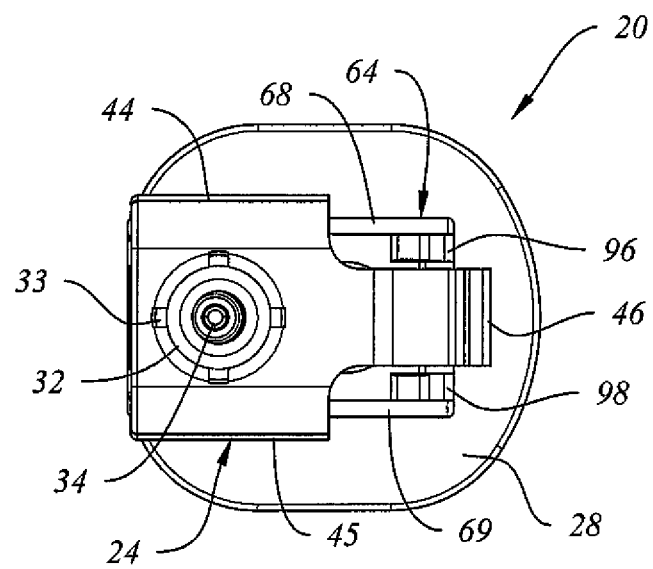
FIG. 13 is a front elevation view of the embodiment of FIG. 12 with the frontal attachment repositioned relative to the barrel and with the needle retracted to the position shown in FIGS. 10 and 11.
Figure 14:
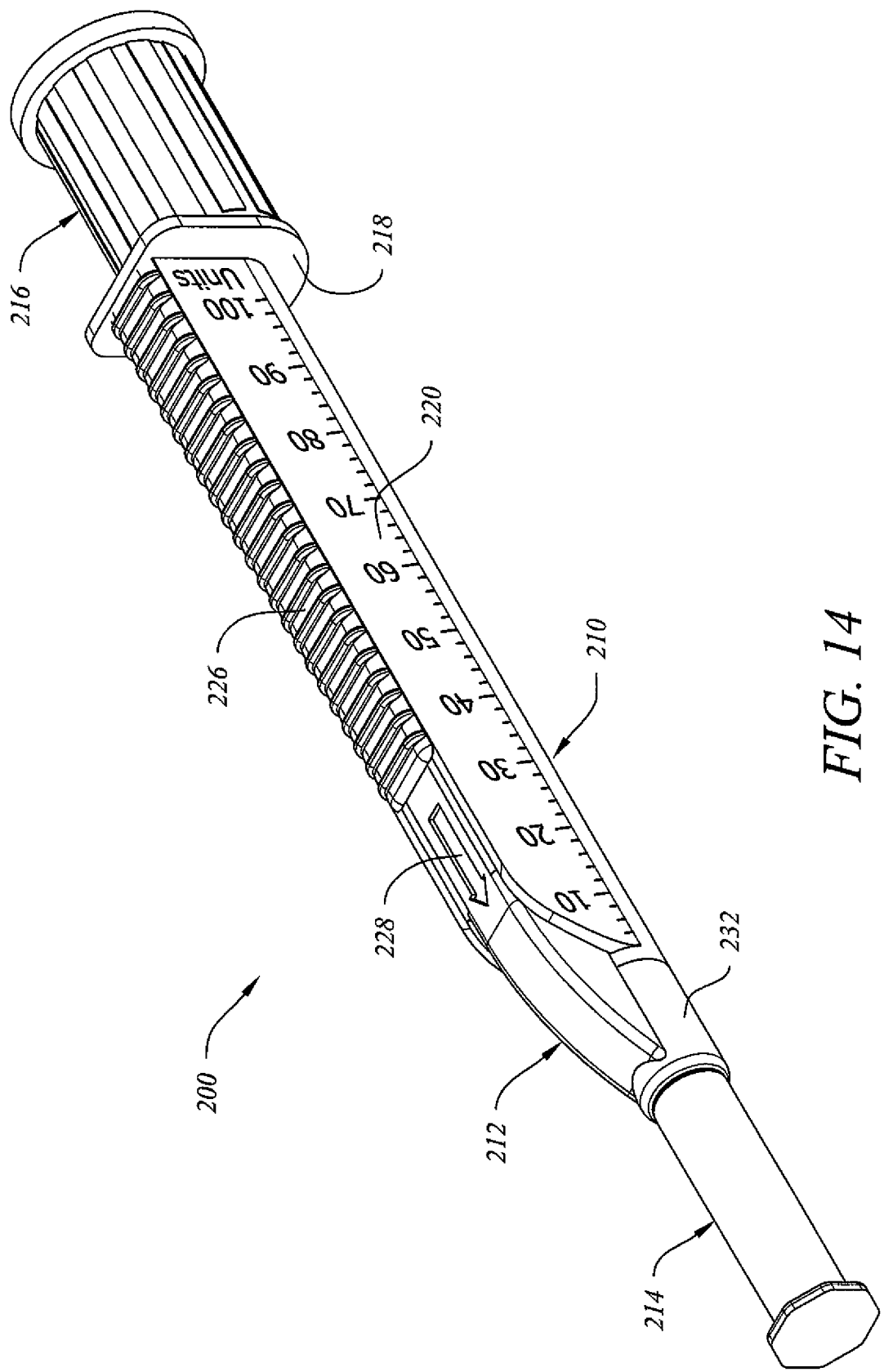
FIG. 14 is a top front perspective view of another embodiment of a syringe of the invention, with both the needle cap and the plunger cap being shown in place as they would be when the syringe is first removed from its packaging.

Referring to FIGS. 10-11 and 13, plunger handle 72 and plunger seal 76 have been pushed forwardly to empty fluid chamber 75. To initiate needle retraction, pressure is applied to textured touch pad 46, which moves frontal attachment to a position where needle support member 32 is aligned with needle retraction cavity 92. Because needle retraction chamber 92 has a front opening that is larger than head 56 of repositioned needle holder 52, the biasing force of compressed spring 52 pushes needle holder 52 rearwardly and causes needle holder 52 and needle 34 to be propelled into the distal end of needle retraction cavity 92.

Referring again to FIGS. 6 and 7, the further application of force to textured touch surface 46 of frontal attachment 24 relative to barrel 22 as described above in relation to FIGS. 10-11 produces sliding relative movement between frontal attachment 24 and front portion 64 of barrel 22. This movement causes upper ramp 104 and lower ramp 106 to slide over the second set of opposed ramps and blocking shoulders 79 so that top and bottom blocking shoulders 108, 110 are placed in facing and abutting contact with upper and lower blocking shoulders 79, thereby preventing frontal attachment 24 from being returned to the use position relative to barrel 22.

Figure 15:
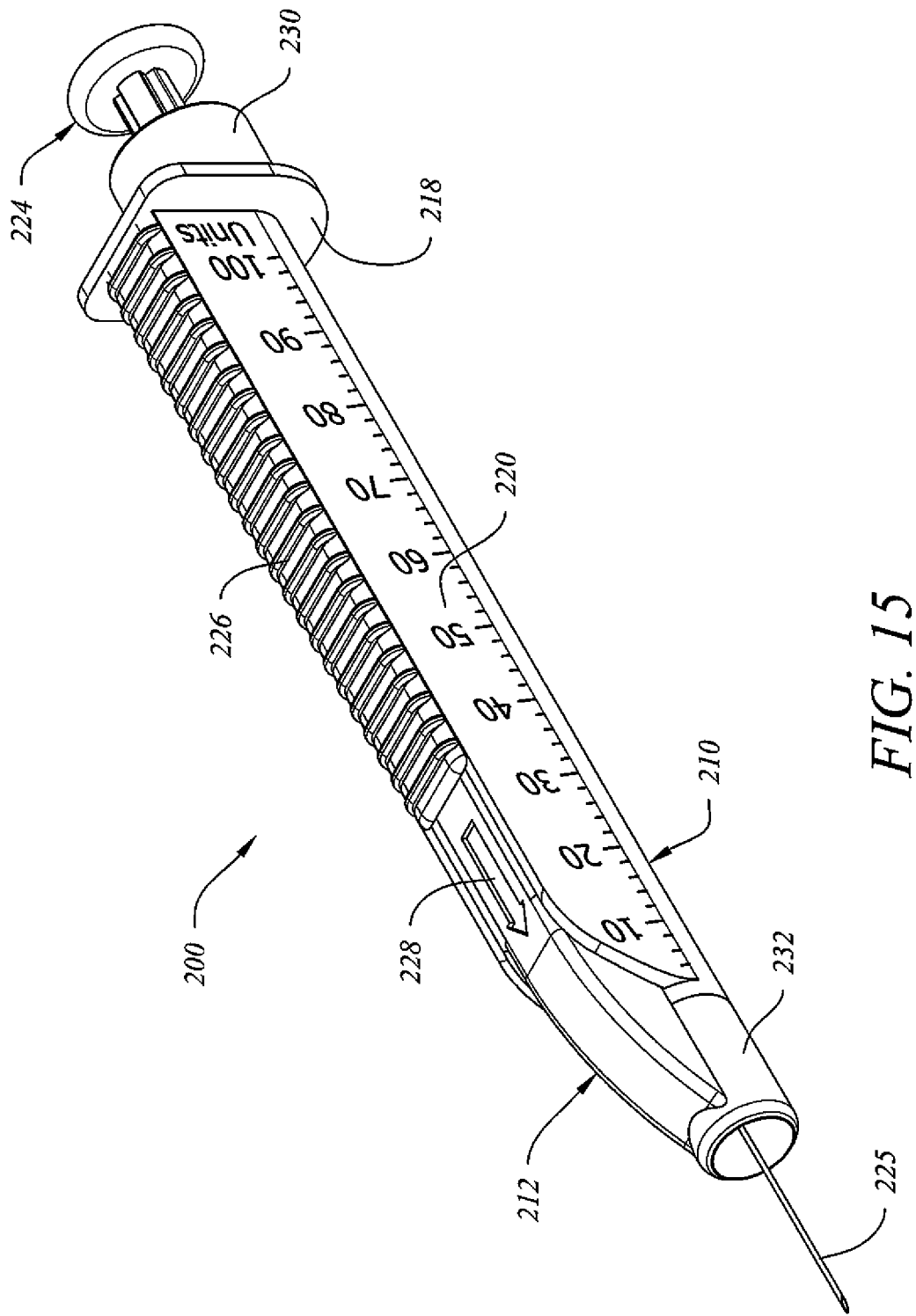
FIG. 15 is the syringe embodiment as shown in FIG. 14 with the needle cap and plunger cap having been removed.
Figure 16:
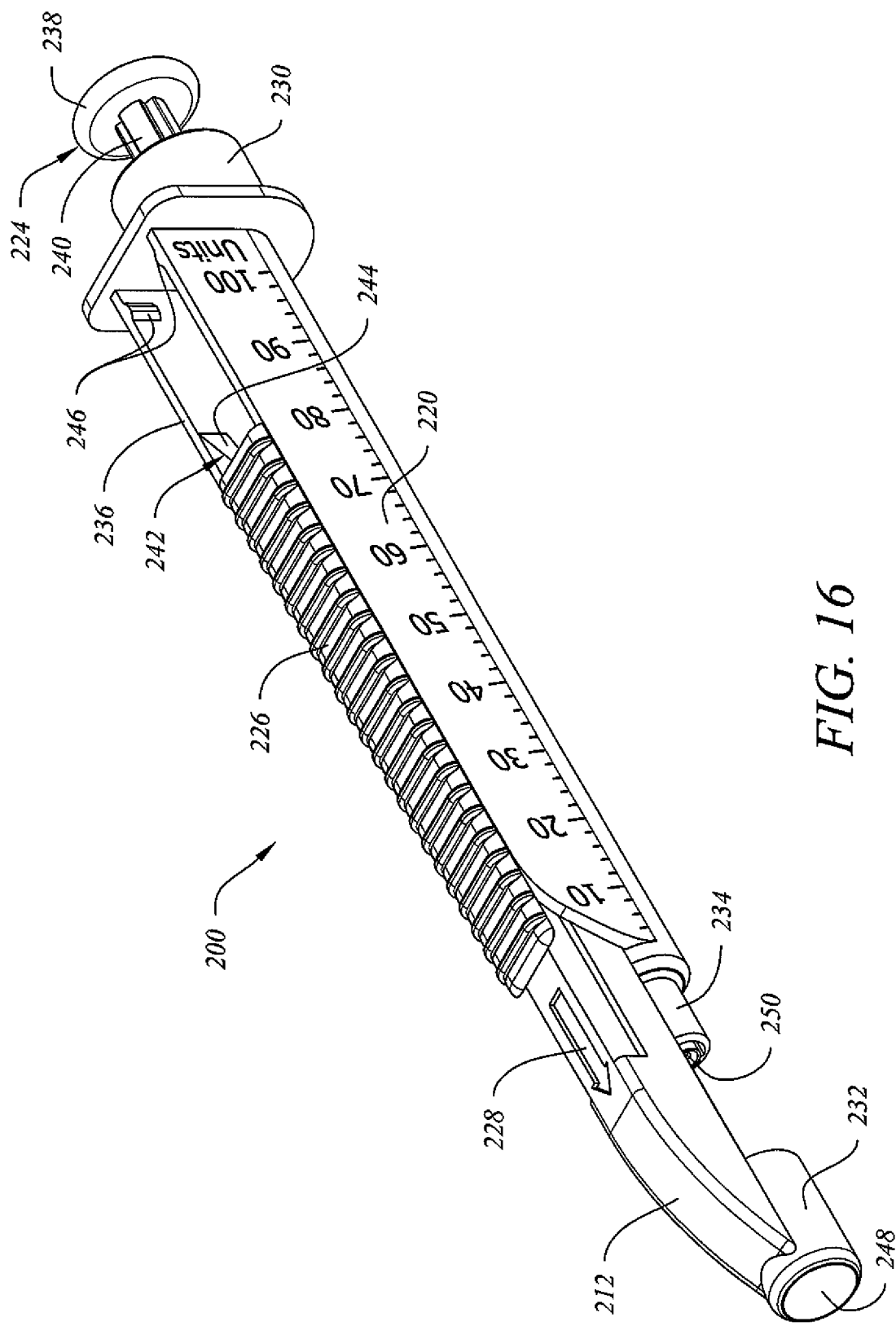
FIG. 16 is the syringe embodiment as shown in FIG. 15 with the needle safety device moved forwardly relative to the barrel and needle, and with the needle tip shield surrounding and covering the needle tip.

Referring to FIGS. 14-24 generally, and specifically to FIGS. 14-17, another embodiment of the invention is disclosed comprising syringe 200 further comprising barrel 210, needle safety device 212, needle cap 214 and plunger cap 216. Barrel 210 desirably comprises at least one longitudinally extending, substantially flat indicia display surface 220 marked with an easily readable volumetric scale. In one preferred embodiment of the invention, barrel 210 comprises two oppositely facing, substantially flat indicia display surfaces 220, 236 (FIG. 16). Following removal of needle cap 214 and plunger cap 216 (FIG. 14) from the device, forwardly projecting needle 225 and rearwardly projecting plunger 224 (FIG. 15) become visible. Needle 225 is coaxially aligned with plunger 224 and is held in fixed relation to a narrow bore 250 inside nose 234 (FIGS. 16, 17, 20) at the front end of barrel 210. (Alternatively, it will be appreciated that needle 225 and nose 234 can be cooperatively configured so that needle 225 is releasably attachable to nose 234 if desired to permit the use of differently sized needles with barrel 234.)

Bore 250 places needle 225 in fluid communication with a fluid reservoir disposed inside tubular barrel 258 between nose 234 and plunger seal 260 on the front end of plunger handle 240. When plunger handle 240 is pushed fully forward against the rear of nose 234 of barrel 210 prior to an injection (FIG. 20) or following an injection (FIG. 23) the fluid chamber is not visible. When syringe 200 is prepared for an injection, as discussed below, the fluid reservoir is the space (not visible in these views) inside tubular section 258 that is between the rear of nose 234 and the front of plunger seal 260 as fluid is drawn into syringe 200.

Figure 17:
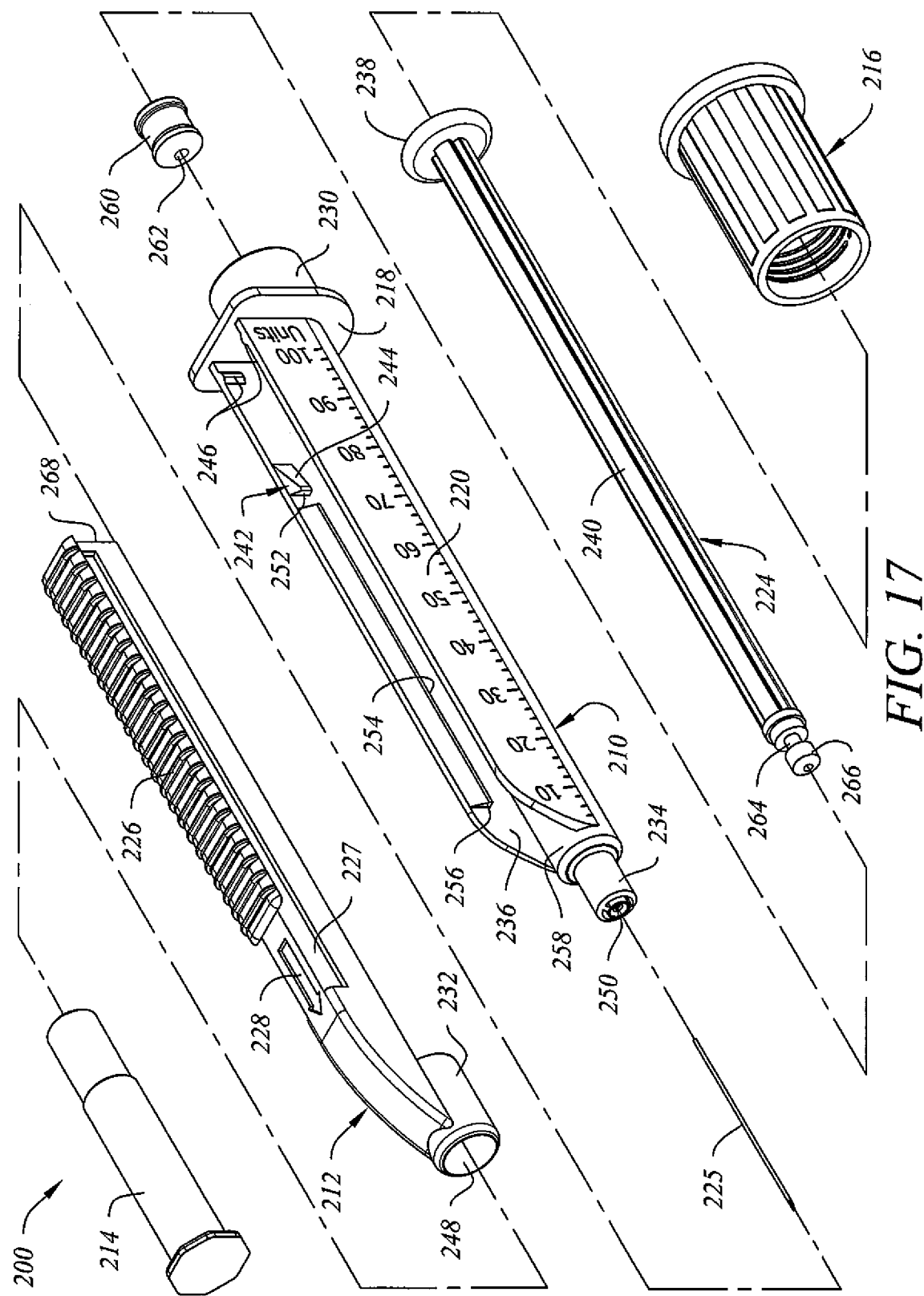
FIG. 17 is an exploded top perspective view of the syringe embodiment of FIG. 14.

Referring to FIG. 17, needle safety device 212 also comprises activation handle 228 and needle tip shield 232. Activation handle 228 further comprises rear end 268, touch pad 226 and a pair of longitudinally extending channels 227 disposed on opposite sides of activation handle 228. The function of channels 227 is discussed below in relation to sliding engagement with barrel 210. Needle tip shield 232 further comprises inside bore 248 that is coaxially aligned with needle 225 and with nose 234 of barrel 210. Needle tip shield 232 desirably has an inside diameter that will allow needle tip shield 232 to slide over and surround coaxially aligned nose 234 when in the position shown in FIGS. 15, 21 and needle tip shield 232 is sufficiently long to safely cover the tip end of needle 225 when moved forwardly as in FIGS. 16, 22-23. Slight frictional engagement can be provided between the inside wall of needle tip shield 232 and nose 234 to help hold needle safety device 212 in a stable axial position relative to barrel 210 during use of syringe 200. Needle safety device 212 is desirably unitarily molded from a polymeric material and is cooperatively sized and configured to slidably engage barrel 210, also taking into consideration the range of needle lengths intended for use with syringe 200.

Referring again to FIG. 17, barrel 210 further comprises coaxially aligned nose 234 with internal bore 250 and tubular section 258 extending rearwardly from nose 234 to fingertip flange 218. The rear end of tubular section 258 is open and communicates with the inside of cylindrical, rearwardly extending collar 230 to which plunger cap 216 is releasably attachable. Opposed indicia display surfaces 220, 236 (FIG. 16) are desirably parallel, longitudinally extending, substantially flat, printable surfaces each having an oppositely facing volumetric scale comprising appropriate indicia located adjacent to tubular section 258 to facilitate easy reading of a liquid level inside tubular section 258 by a user. A longitudinally extending rail 256 with an inwardly projecting retainer edge 254 is desirably provided on the inwardly facing walls of each of the outwardly facing indicia display surfaces 220, 236. Longitudinally extending rails 256 are cooperatively sized and configured to engage and provide a smooth, slidable interface along each of aligned channels 227 of needle safety device 212. Barrel 210 is desirably molded from a medical grade polymeric material and is sufficiently transparent to permit the liquid level drawn into tubular section 258 of syringe 200 to be plainly viewed by a user. Still referring to FIG. 17, plunger 224 further comprises thumb cap 238, plunger handle 240, plunger seal retainer body 266 and annular recess 264.

The cooperatively configured structural elements and operation of needle safety device 212 relative to barrel 210 of syringe 200 are further described and explained in relation to FIGS. 15-17, 20, 22-23. During assembly of syringe 200, activation handle 228 of needle safety device 212 is aligned with and inserted over tubular section 258 of barrel 210 with rails 256 engaging channels 227. Needle safety device 212 is moved rearwardly relative to barrel 210 until needle tip shield 232 surrounds nose 234 of barrel 210 and rear end 268 of needle safety device 212 frictionally engages oppositely disposed rear stops 246. Slide stops 242 each having a ramp 244 and stop shoulder 252 are provided rearwardly of rails 256 and forwardly of rear stops 246. Opposed and facing ramps 244 allow activation handle 228 to slide forwardly relative to barrel 210 to a point where needle tip shield 232 covers and protects the tip end of needle 225 following use of syringe 210. After the tip end of needle 225 is covered, opposed and facing stop shoulders 252 prevent activation handle 228 from being moved rearwardly relative to barrel 210 to again expose the needle tip.

Figure 20:
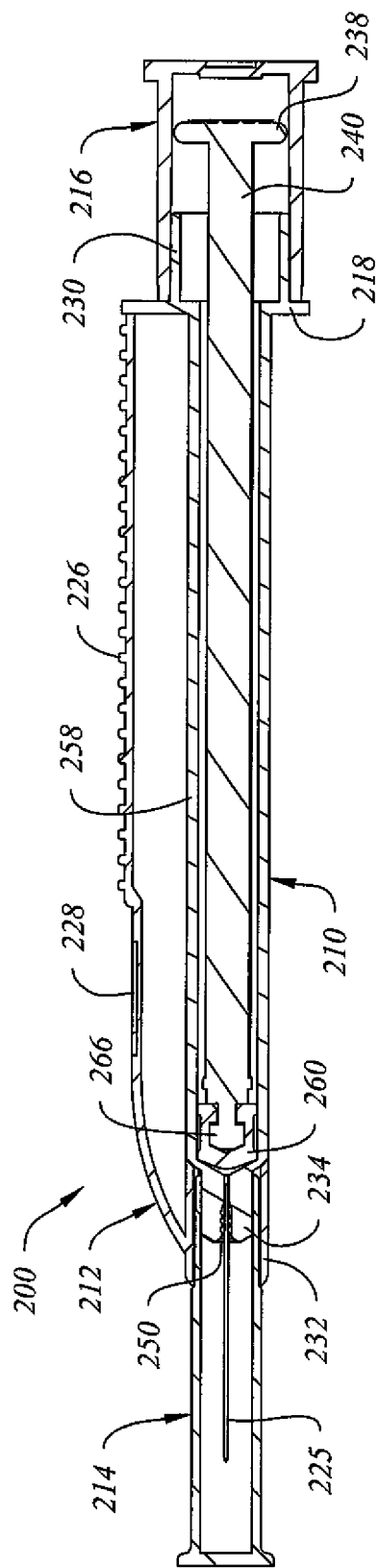
FIG. 20 is a cross-sectional view taken along line 2-2—of FIG. 19.
Figure 21:
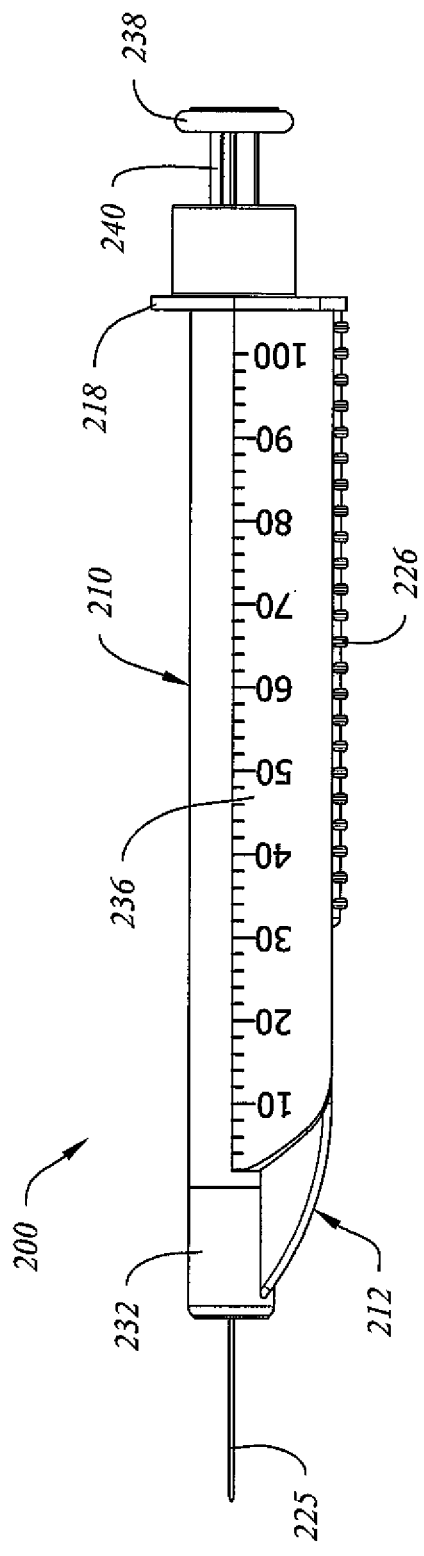
FIG. 21 is the opposite side elevation view of the syringe embodiment as in FIG. 15 but rotated 180° around the longitudinal axis.

When needle safety device 212 and needle tip shield 232 are disposed in the position shown in FIGS. 15, 20-21 (referred to as the "first stop position") relative to barrel 210 and needle 225, needle tip shield 232 surrounds nose 234 of barrel and a portion of needle 225. When needle safety device 212 of syringe 200 is in the first stop position, the front tip of needle 225 can be inserted through the stopper of a medicine vial (e.g., an insulin bottle) and medicine can be drawn into a fluid reservoir disposed inside tubular section 258 (FIGS. 17, 20) of barrel 210 by pulling rearwardly on plunger 224 that slidably engages the inside wall of tubular section 258.

Figure 22:
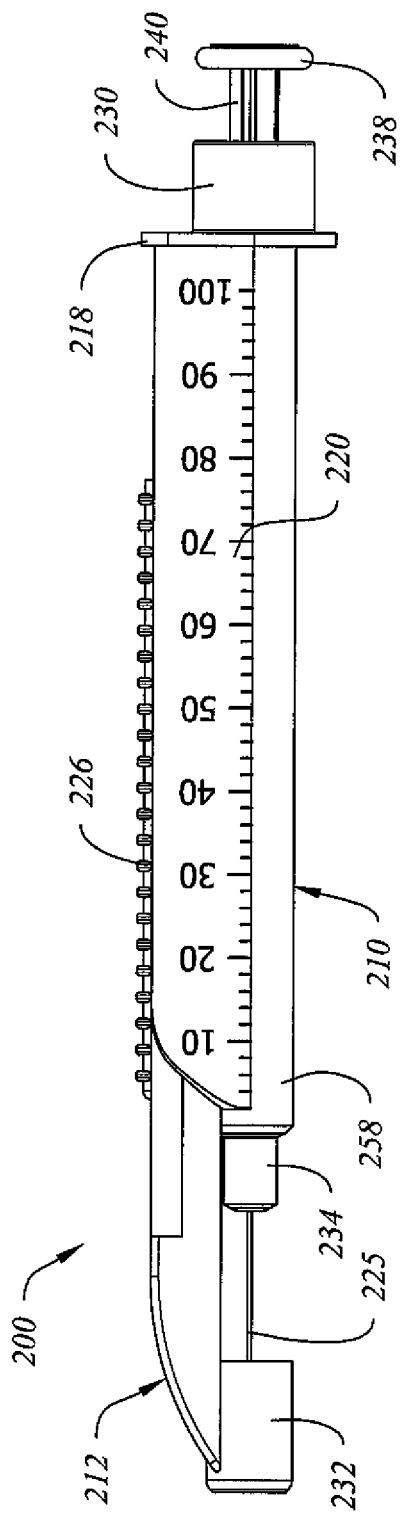
FIG. 22 is a side elevation view of the syringe embodiment as in FIG. 16.
Figure 23:
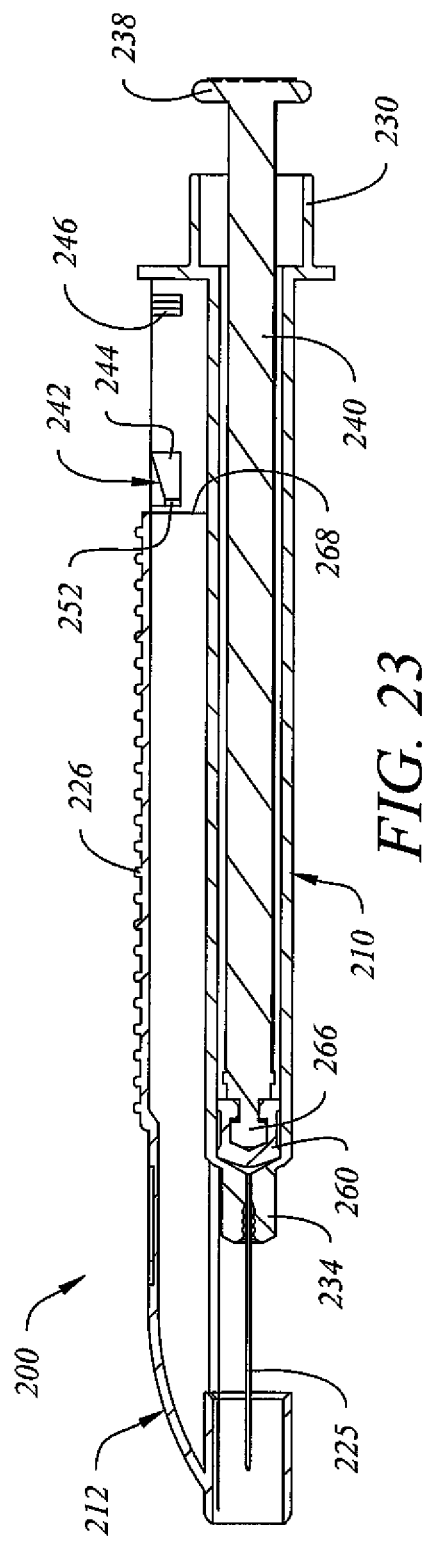
FIG. 23 is a cross-sectional side elevation view taken along the longitudinal axis of the needle of the syringe embodiment as in FIG. 22.
Figure 24:
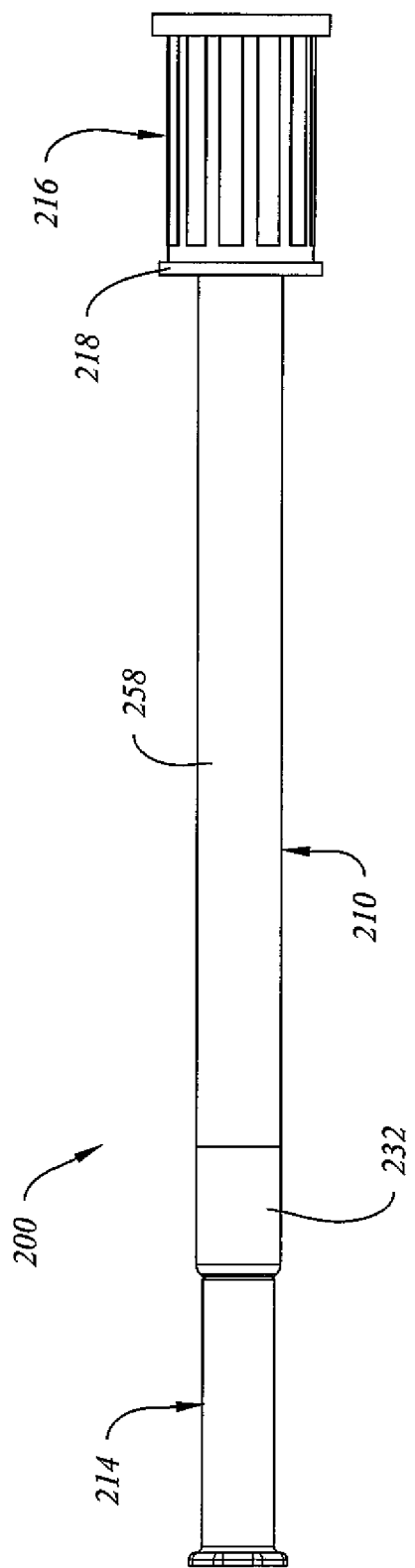
FIG. 24 is a bottom plan view of the syringe embodiment as in FIG. 18.

Following an injection or other use of syringe 200, syringe 200 can be reconfigured into a "safe" position with the needle tip covered and protected from inadvertent contact with a health care professional or patient by selectively moving needle safety device 212 forwardly to the position shown in FIGS. 16, 22-23, which is the "second stop position." When syringe 200 is configured with needle safety device 212 in the second stop position, the front tip of needle 225 is circumferentially surrounded by needle tip shield 232 and (as shown in FIGS. 16, 23) the front end of needle tip shield 232 extends sufficiently forward of the tip end of needle 225 that an individual will not receive an unintended needle stick if the front end of syringe 200 is pressed against his or her skin.

It will become apparent to those of ordinary skill in the art upon reading this specification in relation to the accompanying drawings that various other modifications and alterations can also be made to the embodiments disclosed here, and it is intended that the scope of the invention be limited only by the broadest interpretation of the appended claims to which the inventors are legally entitled.

We claim:

1. A syringe for medical use, comprising:
a barrel comprising (1) a nose with an internal bore, (2) a tubular section extending rearwardly from and coaxially aligned with the nose and having an open rear end, (3) a transversely projecting fingertip flange, and (4) a cylindrical collar extending rearwardly from the transversely projecting fingertip flange and configured to releasably engage with a plunger cap;
a plunger slidably inserted into the tubular section through the cylindrical collar and through the open rear end to form a fluid reservoir inside the tubular section of the barrel;
a needle projecting forwardly from the nose in fixed relation to the internal bore of the nose and in fluid communication with the fluid reservoir;
two indicia display members each unitarily molded and attached in fixed relation to each of the tubular section and the transversely projecting fingertip flange, the two indicia display members each extending longitudinally in a parallel and spaced-apart relation to each other, and each of the two indicia display members having a substantially flat, printable outwardly facing surface, each outwardly facing surface having a printed volumetric scale indicia located adjacent to a sufficiently transparent portion of the tubular section to facilitate reading of a liquid level inside the fluid reservoir through the sufficiently transparent portion of the tubular section; and a needle safety device comprising (1) an activation handle at least partially disposed between and slidably engaging an inwardly facing, longitudinally extending wall of each of the two indicia display members between a first stop position and a "safe" second stop position, and (2) a needle tip shield that surrounds the nose of the barrel in the first stop position and surrounds a front tip of the needle when the activation handle is manually moved forwardly to the "safe" second stop position following use of the syringe.

2. The syringe of claim 1, wherein the printed volumetric scale indicia are applied to the substantially flat outwardly facing surface by pad printing.

3. The syringe of claim 1, wherein the activation handle further comprises a touch surface that is parallel to the tubular section.

4. The syringe of claim 3, wherein at least a portion of the touch surface is disposed adjacent the transversely projecting fingertip flange when the needle safety device is in the first stop position.

5. The syringe of claim 4, wherein at least a portion of the touch surface extends outwardly from the two indicia display members.

6. The syringe of claim 4, wherein at least a portion of the touch surface is disposed rearwardly of a front end of the two indicia display members when the needle safety device is in the "safe" second stop position.

7. The syringe of claim 6, wherein an entirety of the touch surface is disposed rearwardly of the front end of the two indicia display members when the needle safety device is in the first stop position.

8. The syringe of claim 7, wherein none of the printed volumetric scale indicia is disposed on the tubular section.

9. The syringe of claim 1, wherein the activation handle comprises: (1) a touch surface that is longitudinally extending and is parallel to and outwardly spaced apart from the tubular section; (2) a pair of sidewalls extending from the touch surface toward the tubular section; and wherein the needle tip shield extends laterally from a forward end of the pair of sidewalls.

10. The syringe of claim 9, wherein each of the pair of sidewalls contacts an outer surface of the tubular section and allows the activation handle to slidable engage the tubular section.

11. The syringe of claim 1, wherein the activation handle further comprises a pair of longitudinally extending channels disposed on opposite sides of the activation handle, the pair of longitudinally extending channels each being cooperatively sized and configured to slidably engage a longitudinally extending rail having an inwardly projecting retainer edge disposed on the inwardly facing, longitudinally extending wall of each of the two indicia display members.

12. A syringe for medical use comprising:
a fluid chamber comprising a cylindrical sidewall;
a nose disposed at a forward end of the fluid chamber;
a first wall extending laterally outward from the cylindrical sidewall;

a second wall extending laterally outward from the cylindrical sidewall and parallel to the first wall;

a volumetric scale indicia disposed on an outwardly facing surface of the first wall and disposed adjacent to the cylindrical sidewall, wherein no volumetric scale indicia is disposed on the cylindrical sidewall;

a needle in fluid communication with the fluid chamber and projecting forwardly from the nose; and a needle safety device configured to slide forwardly between the first wall and the second wall from a first stop position in which a front tip of the needle is exposed and a second stop position in which the front tip of the needle is circumferentially covered by a portion of the needle safety device;

wherein the first wall and the second wall extend laterally outward from the cylindrical sidewall in a single direction, and wherein the first wall, the second wall, and the cylindrical sidewall are unitarily molded.

13. The syringe of claim 12, wherein the needle safety device comprises a longitudinal touch pad that is disposed parallel to the cylindrical sidewall.

14. The syringe of claim 12, wherein the first wall and the second wall extend longitudinally along the cylindrical sidewall.

15. The syringe of claim 12, further comprising a finger flange disposed at a rear end of the fluid chamber and wherein a rear end of the first wall and a rear end of the second wall are disposed adjacent to or abutting the finger flange.

16. The syringe of claim 15, wherein at least a portion of a rear facing end of the needle safety device is disposed between the first wall and the second wall as the needle safety device slides from the first stop position to the second stop position.

17. A syringe for medical use, comprising:
a fluid chamber comprising a tubular sidewall extending longitudinally;

a display extending longitudinally and disposed in fixed relation to the fluid chamber, the display comprising a first wall unitarily molded to the tubular sidewall, a second wall unitarily molded to the tubular sidewall and extending in parallel to the first wall, and a volumetric scale indicia;

a first channel formed between the first wall, the second wall, and a portion of the tubular sidewall;

a needle disposed at a forward end of the syringe and in fluid communication with the fluid chamber;

a needle safety device comprising a needle tip shield, an activation handle disposed rearwardly of the needle tip shield, and a touch pad disposed on an outwardly facing surface of the activation handle parallel with the tubular sidewall, and wherein a least a first portion of the activation handle is disposed within the first channel;

a pair of sliding rails disposed on the first wall and the second wall; and a pair of sliding channels disposed in the needle safety device;

wherein the pair of sliding channels are configured to slidably engage with the pair of sliding rails to allow the needle safety device to slide between a first stop position and a second stop position relative to the first channel;

wherein a front tip of the needle is exposed when the needle safety device is disposed in the first stop position;

wherein the needle tip shield circumferentially surrounds the front tip of the needle when the needle safety device is moved forwardly from the first stop position to the second stop position; and wherein the volumetric scale indicia are disposed on a substantially flat outwardly facing surface of the first wall, the second wall, or both.

18. The syringe of claim 17, wherein a first of the pair of sliding rails is disposed on an inwardly facing surface of the first wall and a second of the pair of sliding rails is disposed on an inwardly facing surface of the second wall substantially opposite the first of the pair of sliding rails.

19. The syringe of claim 18, wherein a first of the pair of sliding channels is disposed on a first side of the activation handle inwardly of the touch pad and a second of the pair of sliding channels is disposed on a second side of the activation handle inwardly of the touch pad and substantially opposite from the first of the pair of sliding channels.

20. The syringe of claim 19, further comprising at least one slide stop, wherein subsequent rearward movement of the needle safety device after being in the second stop position is prevented by the at least one slide stop abutting a rear end of the activation handle, and wherein the at least one slide stop is disposed rearwardly of the pair of sliding rails.

21. The syringe of claim 19, further comprising a first slide stop disposed rearwardly of the first of the pair of sliding rails and a second slide stop disposed rearwardly of the second of the pair of sliding rails and wherein each of the pair of sliding rails comprises an inwardly projecting retaining edge.

22. The syringe of claim 17, wherein the volumetric scale indicia are applied to the substantially flat outwardly facing surface of the first wall, or of the second wall, or both by pad printing.

23. The syringe of claim 17, wherein at least a portion of the touch pad extends outwardly from the first channel.

24. The syringe of claim 17, wherein tubular sidewall and the display are unitarily molded as a single piece.

25. The syringe of claim 17, further comprising a finger flange disposed rearwardly of the fluid chamber and the display and extending outwardly; and wherein a rear end of the activation handle or a rear end of the touch pad abuts the finger flange when the needle safety device is in the first stop position.

26. The syringe of claim 17, wherein the volumetric scale indicia is disposed offset from a centerline of the fluid chamber such that the volumetric scale indicia does not interfere with reading of a liquid level inside the fluid chamber through a portion of the tubular sidewall adjacent the volumetric scale indicia.

27. The syringe of claim 26, wherein the portion of the tubular sidewall adjacent the volumetric scale indicia is sufficiently transparent to allow the liquid level to be directly visible through the portion of the tubular sidewall.

28. The syringe of claim 17, wherein the volumetric scale indicia is only disposed on the display and not on the tubular sidewall.

29. The syringe of claim 17, wherein the needle safety device does not comprise a spring.

30. The syringe of claim 17, wherein the volumetric scale indicia is partially disposed on the display and partially disposed on the tubular sidewall.

31. The syringe of claim 17, wherein the first wall and the second wall extend to only one side of the fluid chamber.

* * * * *